United States Patent [19]

Christiansen et al.

[11] Patent Number: 5,726,038
[45] Date of Patent: Mar. 10, 1998

[54] DNA CONSTRUCT ENCODING THE YAP3 SIGNAL PEPTIDE

[75] Inventors: Lars Christiansen, Lyngby; Jens Gunner Litske Petersen, Valby, both of Denmark

[73] Assignee: Novo Nordisk A/S, Bagsvaerd, Denmark

[21] Appl. No.: 446,646

[22] PCT Filed: Jul. 8, 1994

[86] PCT No.: PCT/DK94/00281

§ 371 Date: May 25, 1995

§ 102(e) Date: May 25, 1995

[87] PCT Pub. No.: WO95/02059

PCT Pub. Date: Jan. 19, 1995

[30] Foreign Application Priority Data

Jul. 8, 1993 [DK] Denmark ................. 0828/93

[51] Int. Cl.$^6$ ................. C12N 15/00
[52] U.S. Cl. ................. 435/69.1; 435/69.4; 435/71.1; 435/254.11; 435/255.2; 435/320.1; 536/23.1; 536/23.5; 536/23.51
[58] Field of Search ................. 435/69.1, 172.3, 435/91, 70, 256, 255, 240.2, 320.1, 252.3, 71, 71.1, 226, 254.2, 21, 69.4, 254.11, 255.2; 536/27, 23.4, 23.2, 23.5, 23.51, 23.1

[56] References Cited

U.S. PATENT DOCUMENTS

| | | | |
|---|---|---|---|
| 5,037,743 | 8/1991 | Welch et al. | 435/69.1 |
| 5,217,891 | 6/1993 | Brake et al. | 435/226 |
| 5,538,863 | 7/1996 | Price | 435/69.1 |

FOREIGN PATENT DOCUMENTS

WO 87/02670  5/1987  WIPO .

OTHER PUBLICATIONS

Egel–Mitani, M. 1990 Yeast 6:127–137.
J. Cellular Biochem., vol. 12, (1988) Suppl. O. Part B.

Primary Examiner—James Ketter
Assistant Examiner—Irem Yucel
Attorney, Agent, or Firm—Steve T. Zelson, Esq.; Valeta Gregg, Esq.

[57] ABSTRACT

A DNA construct comprising the following sequence: 5'-P-SP-(LP)$_n$-PS-HP-3' wherein P is a promoter sequence, SP is a DNA sequence encoding the yeast aspartic protease 3 (YAP3) signal peptide, LP is a DNA sequence encoding a leader peptide, n is 0 or 1, PS is a DNA sequence encoding a peptide defining a yeast processing site, and HP is a DNA sequence encoding a polypeptide which is heterologous to a selected host organism. The YAP3 signal peptide provides efficient secretion of heterologous proteins in yeast.

16 Claims, 13 Drawing Sheets

```
           10        20        30        40        50        60
            |         |         |         |         |         |
GGAATTCATTCAAGAATAGTTCAAACAAGAAGATTACAAACTATCAATTTCATACACAAT 70        80        90       100       110       120
            |         |         |         |         |         |
ATAAACGACGGTACCAAAATAATGAAACTGAAAACTGTAAGATCTGCGGTCCTTTCGTCA
                      METLysLeuLysThrValArgSerAlaValLeuSerSer
                     ----------------YAP3_SP----------------

130       140       150       160       170       180
            |         |         |         |         |         |
CTCTTTGCATCTCAGGTCCTTGGCCAACCAATAGACACGCGTAAAGAAGGCCTACAGCAT
LeuPheAlaSerGlnValLeuGlyGlnProIleAspThrArgLysGluGlyLeuGlnHis
---------------------------*********************************

190       200       210       220       230       240
            |         |         |         |         |         |
GATTACGATACAGAGATCTTGGAGCACATTGGAAGCGATGAGTTAATTTTGAATGAAGAG
AspTyrAspThrGluIleLeuGluHisIleGlySerAspGluLeuIleLeuAsnGluGlu
***************  63.15d3 leader  ***************************

250       260       270       280       290       300
            |         |         |         |         |         |
TATGTTATTGAAAGAACTTTGCAAGCCATCGATAACACCACTTTGGCTAAGAGATTCGTT
TyrValIleGluArgThrLeuGlnAlaIleAspAsnThrThrLeuAlaLysArgPheVal
*******************************************************>>>>>

310       320       330       340       350       360
            |         |         |         |         |         |
AACCAACACTTGTGCGGTTCCCACTTGGTTGAAGCTTTGTACTTGGTTTGCGGTGAAAGA
AsnGlnHisLeuCysGlySerHisLeuValGluAlaLeuTyrLeuValCysGlyGluArg
>>>>>>>>>>>>>>>>>  Insulin precursor MI3  >>>>>>>>>>>>>>>>>>>

370       380       390       400       410       420
            |         |         |         |         |         |
GGTTTCTTCTACACTCCTAAGGCTGCTAAGGGTATTGTCGAACAATGCTGTACCTCCATC
GlyPhePheTyrThrProLysAlaAlaLysGlyIleValGluGlnCysCysThrSerIle
>>>>>>>>>>>>>>>>>>>>>>>>>>>>>>>>>>>>>>>>>>>>>>>>>>>>>>>>>>>>

430       440       450       460       470
            |         |         |         |         |
TGCTCCTTGTACCAATTGGAAAACTACTGCAACTAGACGCAGCCCGCAGGCTCTAGA
CysSerLeuTyrGlnLeuGluAsnTyrCysAsn---
>>>>>>>>>>>>>>>>>>>>>>>>>>>>>>>>>
```

Fig. 2

```
         10        20        30        40        50        60
          |         |         |         |         |         |
GAATTCATTCAAGAATAGTTCAAACAAGAAGATTACAAACTATCAATTTCATACACAATA 70        80        90       100       110       120
          |         |         |         |         |         |
TAAACGATTAAAAGAATGAAGGCTGTTTTCTTGGTTTTGTCCTTGATCGGATTCTGCTGG
                  METLysAlaValPheLeuValLeuSerLeuIleGlyPheCysTrp
                  ------------------- spx 3 --------------

130       140       150       160       170       180
          |         |         |         |         |         |
GCCCAACCATCGAAATTGAAACCAGCTAGCGATATACAAATTCTTTACGACCATGGTGTG
AlaGlnProSerLysLeuLysProAlaSerAspIleGlnIleLeuTyrAspHisGlyVal
---

190       200       210       220       230       240
          |         |         |         |         |         |
AGGGAGTTCGGGGAAAACTATGTTCAAGAGTTGATCGATAACACCACTTTGGCTAACGTC
ArgGluPheGlyGluAsnTyrValGlnGluLeuIleAspAsnThrThrLeuAlaAsnVal 250       260       270       280       290       300
          |         |         |         |         |         |
GCCATGGCTGAGAGATTGGAGAAGAGAAGGCCTGATTTCTGTTTGGAACCTCCATACACT
AlaMetAlaGluArgLeuGluLysArgArgProAspPheCysLeuGluProProTyrThr
                              >>>>>>>>>>>>>>>>>>>>>>>>>>>>>>

310       320       330       340       350       360
          |         |         |         |         |         |
GGTCCATGTAAAGCTAGAATCATCAGATACTTCTACAACGCCAAGGCTGGTTTGTGTCAA
GlyProCysLysAlaArgIleIleArgTyrPheTyrAsnAlaLysAlaGlyLeuCysGln
>>>>>>>>>>>>>>> Aprotinin >>>>>>>>>>>>>>>>>>>>>>>>>>>>>>>>>>

370       380       390       400       410       420
          |         |         |         |         |         |
ACTTTCGTTTACGGTGGCTGCAGAGCTAAGAGAAACAACTTCAAGTCTGCTGAAGACTGC
ThrPheValTyrGlyGlyCysArgAlaLysArgAsnAsnPheLysSerAlaGluAspCys
>>>>>>>>>>>>>>>>>>>>>>>>>>>>>>>>>>>>>>>>>>>>>>>>>>>>>>>>>>>>

430       440       450
          |         |         |
ATGAGAACTTGTGGTGGTGCCTAATCTAGA
METArgThrCysGlyGlyAla---
>>>>>>>>>>>>>>>>>>>>>>
```

Fig. 4

```
         10         20         30         40         50         60
          |          |          |          |          |          |
GGAATTCATTCAAGAATAGTTCAAACAAGAAGATTACAAACTATCAATTTCATACACAAT 70         80         90        100        110        120
          |          |          |          |          |          |
ATAAACGACGGTACCAAAATAATGAAACTGAAAACTGTAAGATCTGCGGTCCTTTCGTCA
                      METLysLeuLysThrValArgSerAlaValLeuSerSer
                      ---------------- YAP3_SP ---------------

130        140        150        160        170        180
          |          |          |          |          |          |
CTCTTTGCATCTCAGGTCCTTGGCCAACCATCGAAATTGAAACCAGCTAGCGATATACAA
LeuPheAlaSerGlnValLeuGlyGlnProSerLysLeuLysProAlaSerAspIleGln
---------------------------

190        200        210        220        230        240
          |          |          |          |          |          |
ATTCTTTACGACCATGGTGTGAGGGAGTTCGGGGAAAACTATGTTCAAGAGTTGATCGAT
IleLeuTyrAspHisGlyValArgGluPheGlyGluAsnTyrValGlnGluLeuIleAsp 250        260        270        280        290        300
          |          |          |          |          |          |
AACACCACTTTGGCTAACGTCGCCATGGCTGAGAGATTGGAGAAGAGAAGGCCTGATTTC
AsnThrThrLeuAlaAsnValAlaMetAlaGluArgLeuGluLysArgArgProAspPhe
                                                   >>>>>>>>>>>

310        320        330        340        350        360
          |          |          |          |          |          |
TGTTTGGAACCTCCATACACTGGTCCATGTAAAGCTAGAATCATCAGATACTTCTACAAC
CysLeuGluProProTyrThrGlyProCysLysAlaArgIleIleArgTyrPheTyrAsn
>>>>>>>>>>>>>> Aprotinin >>>>>>>>>>>>>>>>>>>>>>>>>>>>>>>>>>>>

370        380        390        400        410        420
          |          |          |          |          |          |
GCCAAGGCTGGTTTGTGTCAAACTTTCGTTTACGGTGGCTGCAGAGCTAAGAGAAACAAC
AlaLysAlaGlyLeuCysGlnThrPheValTyrGlyGlyCysArgAlaLysArgAsnAsn
>>>>>>>>>>>>>>>>>>>>>>>>>>>>>>>>>>>>>>>>>>>>>>>>>>>>>>>>>>>>>

430        440        450        460        470
          |          |          |          |          |
TTCAAGTCTGCTGAAGACTGCATGAGAACTTGTGGTGGTGCCTAATCTAGA
PheLysSerAlaGluAspCysMetArgThrCysGlyGlyAla---
>>>>>>>>>>>>>>>>>>>>>>>>>>>>>>>>>>>>>>>>>
```

Fig. 6

```
SalI                                                      NheI
GTCGACC ATG ATT TAC ACA ATG AAG AAA GTA CAT GCA CTT TGG GCT AGC         49
        Met Ile Tyr Thr Met Lys Lys Val His Ala Leu Trp Ala Ser
        -28         -25             -20                 -15

GTA TGC CTG CTG CTT AAT CTT GCC CCT GCC CCT CTT AAT GCT GAT TCT         97
Val Cys Leu Leu Leu Asn Leu Ala Pro Ala Pro Leu Asn Ala Asp Ser
            -10             -5                          1

SacI
GAG GAA GAT GAA GAA CAC ACA ATT ATC ACA GAT ACG GAG CTC CCA CCA         145
Glu Glu Asp Glu Glu His Thr Ile Ile Thr Asp Thr Glu Leu Pro Pro
        5               10                  15

ApaI
CTG AAA CTT ATG CAT TCA TTT TGT GCA TTC AAG GCG GAT GAT GGG CCC         193
Leu Lys Leu Met His Ser Phe Cys Ala Phe Lys Ala Asp Asp Gly Pro
    20              25                  30

TGT AAA GCA ATC ATG AAA AGA TTT TTC TTC AAT ATT TTC ACT CGA CAG         241
Cys Lys Ala Ile Met Lys Arg Phe Phe Phe Asn Ile Phe Thr Arg Gln
35              40                  45                      50

ClaI
TGC GAA GAA TTT ATA TAT GGG GGA TGT GAA GGA AAT CAG AAT CGA TTT         289
Cys Glu Glu Phe Ile Tyr Gly Gly Cys Glu Gly Asn Gln Asn Arg Phe
                55              60                  65

GAA AGT CTG GAA GAG TGC AAA AAA ATG TGT ACA AGA GAT AAT GCA AAC         337
Glu Ser Leu Glu Glu Cys Lys Lys Met Cys Thr Arg Asp Asn Ala Asn
            70              75                  80

AGG ATT ATA AAG ACA ACA CTG CAG CAA GAA AAG CCA GAT TTC TGC TTT         385
Arg Ile Ile Lys Thr Thr Leu Gln Gln Glu Lys Pro Asp Phe Cys Phe
        85              90                  95

BamHI
TTG GAA GAG GAT CCT GGA ATA TGT CGA GGT TAT ATT ACC AGG TAT TTT         433
Leu Glu Glu Asp Pro Gly Ile Cys Arg Gly Tyr Ile Thr Arg Tyr Phe
    100             105                 110

ΔStuI
TAT AAC AAT CAG ACA AAA CAG TGT GAA AGG TTC AAG TAT GGT GGA TGC         481
Tyr Asn Asn Gln Thr Lys Gln Cys Glu Arg Phe Lys Tyr Gly Gly Cys
115             120                 125                 130

XhoI
CTG GGC AAT ATG AAC AAT TTT GAG ACA CTC GAG GAA TGC AAG AAC ATT         529
Leu Gly Asn Met Asn Asn Phe Glu Thr Leu Glu Glu Cys Lys Asn Ile
            135                 140                 145
```

Fig. 7a

```
                                                    KnpI
TGT GAA GAT GGT CCG AAT GGT TTC CAG GTG GAT AAT TAT GGT ACC CAG         577
Cys Glu Asp Gly Pro Asn Gly Phe Gln Val Asp Asn Tyr Gly Thr Gln
            150                 155                 160

HpaI
CTC AAT GCT GTT AAC AAC TCC CTG ACT CCG CAA TCA ACC AAG GTT CCC         625
Leu Asn Ala Val Asn Asn Ser Leu Thr Pro Gln Ser Thr Lys Val Pro
            165                 170                 175

EcoRI
AGC CTT TTT GAA TTC CAC GGT CCC TCA TGG TGT CTC ACT CCA GCA GAT         673
Ser Leu Phe Glu Phe His Gly Pro Ser Trp Cys Leu Thr Pro Ala Asp
            180                 185                 190

ΔEcoRV
AGA GGA TTG TGT CGT GCC AAT GAG AAC AGA TTC TAC TAC AAT TCA GTC         721
Arg Gly Leu Cys Arg Ala Asn Glu Asn Arg Phe Tyr Tyr Asn Ser Val
195                 200                 205                 210

BspMII
ATT GGG AAA TGC CGC CCA TTT AAG TAC TCC GGA TGT GGG GGA AAT GAA         769
Ile Gly Lys Cys Arg Pro Phe Lys Tyr Ser Gly Cys Gly Gly Asn Glu
            215                 220                 225

SpeI                            SphI
AAC AAT TTT ACT AGT AAA CAA GAA TGT CTG AGG GCA TGC AAA AAA GGT         817
Asn Asn Phe Thr Ser Lys Gln Glu Cys Leu Arg Ala Cys Lys Lys Gly
            230                 235                 240

StuI
TTC ATC CAA AGA ATA TCA AAA GGA GGC CTA ATT AAA ACC AAA AGA AAA         865
Phe Ile Gln Arg Ile Ser Lys Gly Gly Leu Ile Lys Thr Lys Arg Lys
            245                 250                 255

AGA AAG AAG CAG AGA GTG AAA ATA GCA TAT GAA GAA ATT TTT GTT AAA         913
Arg Lys Lys Gln Arg Val Lys Ile Ala Tyr Glu Glu Ile Phe Val Lys
            260                 265                 270

SalI
AAT ATG TGAGTCGAC                                                        928
Asn Met
275
```

Fig. 7b

```
          EcoRI
5361 GAATTCATTCAAGAATAGTTCAAACAAGAAGATTACAAACTATCAATTTCATACACAAT

5420 ATAAACGATTAAAAGAATGAAGGCTGTTTTCTTGGTTTTGTCCTTGATCGGATTCTGCT
                      MetLysAlaValPheLeuValLeuSerLeuIleGlyPheCys
                      ---------------spx3 signal peptide-------

PfIMI                                BspEI          BclI
5479 GGGCCCAACCAGTCACTGGCGATGAATCATCTGTTGAGATTCCGGAAGAGTCTCTGATC
     TrpAlaGlnProValThrGlyAspGluSerSerValGluIleProGluGluSerLeuIle
     ---------+++++++++++++++++++++++++++++++212 leader ++++++++++++++

5438 ATCGCTGAAAACACCACTTTGGCTAACGTCGCCATGGCTAAGAGAGATTCTGAGGAA
     IleAlaGluAsnThrThrLeuAlaAsnValAlaMetAlaLysArgAspSerGluGlu--
     ++++++++++++++++++++++++++++++++++++++++++++++++<- TFPI   --
                                                  Kex2
```

Fig. 8a

```
         EcoRI              HindIII        BglII
5361 GAATTCAAACTAAAAAATGAAGCTTAAAACTGTAAGATCTGCGGTCCTTTCGTCACTCT
                        MetLysLeuLysThrValArgSerAlaValLeuSerSerLeu
                        -----------Yap3 signal peptide----------

AvrII    PfIMI                                BspEI
5420 TTGCATCGCAGGTCCTAGGTCAACCAGTCACTGGCGATGAATCATCTGTTGAGATTCCG
     PheAlaSerGlnValLeuGlyGlnProValThrGlyAspGluSerSerValGluIlePro
     ---------------------+++++++++++++212 leader+++++++++++++++

BclI                                   NcoI
5479 GAAGAGTCTCTGATCATCGCTGAAAACACCACTTTGGCTAACGTCGCCATGGCTAAGAG
     GluGluSerLeuIleIleAlaGluAsnThrThrLeuAlaAsnValAlaMetAlaLys
     ++++++++++++++++++++++++++++++++++++++++++++++++++++++++++

5538 AGATTCTGAGGAA--
     ArgAspSerGluGlu--
     +++<-TFPI  --
```

Fig. 8b

DNA CONSTRUCT ENCODING THE YAP3 SIGNAL PEPTIDE

CROSS-REFERENCE TO RELATED APPLICATIONS

This application is a of PCT/DK94/00281 filed Jul. 8, 1994, which is incorporated herein by reference.

FIELD OF INVENTION

The present invention relates to a DNA construct comprising the YAP3 signal peptide for secretion of a heterologous polypeptide, a yeast cell containing the DNA construct and a method of producing heterologous polypeptides in yeast from the DNA construct.

BACKGROUND OF THE INVENTION

Yeast organisms produce a number of proteins which are synthesized intracellularly, but which have a function outside the cell. Such extracellular proteins are referred to as secreted proteins. These secreted proteins are expressed initially inside the cell in a precursor or a pre-protein form containing a presequence ensuring effective direction of the expressed product across the membrane of the endoplasmic reticulum (ER). The presequence, normally named a signal peptide, is cleaved off from the rest of the protein during translocation. Once entered in the secretory pathway, the protein is transported to the Golgi apparatus. From the Golgi the protein can follow different routes that lead to compartments such as the cell vacuole or the cell membrane, or it can be routed out of the cell to be secreted to the external medium (Pfeffer, S. R. and Rothman, J. E. *Ann. Rev. Biochem.* 56 (1987), 829–852).

Several approaches have been suggested for the expression and secretion in yeast of proteins heterologous to yeast. European published patent application No. 88 632 describes a process by which proteins heterologous to yeast are expressed, processed and secreted by transforming a yeast organism with an expression vehicle harbouring DNA encoding the desired protein and a signal peptide, preparing a culture of the transformed organism, growing the culture and recovering the protein from the culture medium. The signal peptide may be the signal peptide of the desired protein itself, a heterologous signal peptide or a hybrid of native and heterologous signal peptide.

A problem encountered with the use of signal peptides heterologous to yeast might be that the heterologous signal peptide does not ensure efficient translocation and/or cleavage after the signal peptide.

The *S. cerevisiae* MFα1 (α-factor) is synthesized as a prepro form of 165 amino acids comprising signal-or prepeptide of 19 amino acids followed by a "leader" or propeptide of 64 amino acids, encompassing three N-linked glycosylation sites followed by (LysArg(Asp/Glu, Ala)$_{2-3}$α-factor)$_4$ (Kurjan, J. and Herskowitz, I. *Cell* 30 (1982), 933–943). The signal-leader part of the preproMFα1 has been widely employed to obtain synthesis and secretion of heterologous proteins in *S. cerivisiae*.

Use of signal/leader peptides homologous to yeast is known from i.a. U.S. Pat. No. 4,546,082, European published patent applications Nos. 116 201, 123 294, 123 544, 163 529, and 123 289 and DK patent application No. 3614/83.

In EP 123 289 utilization of the *S. cerevisiae* a-factor precursor is described whereas WO 84/01153 indicates utilization of the *Saccharomyces cerevisiae* invertase signal peptide and DK 3614/83 utilization of the *Saccharomyces cerevisiae* PH05 signal peptide for secretion of foreign proteins.

U.S. Pat. No. 4,546,082, EP 16 201, 123 294,123 544, and 163 529 describe processes by which the α-factor signal-leader from *Saccharomyces cerevisiae* (MFα1 or MFα2) is utilized in the secretion process of expressed heterologous proteins in yeast. By fusing a DNA sequence encoding the *S. cerevisiea* MFα1 signal/leader sequence at the 5' end of the gene for the desired protein secretion and processing of the desired protein was demonstrated.

A number of secreted proteins are routed so as to be exposed to a proteolytic processing system which can cleave the peptide bond at the carboxy end of two consecutive basic amino acids. This enzymatic activity is in *S. cerevisiae* encoded by the KEX 2 gene (Julius, D. A. et al., *Cell* 37 (1984b), 1075). Processing of the product by the KEX 2 gene product is needed for the secretion of active *S. cerevisiae* mating factor α (MFα or α-factor) but is not involved in the secretion of active *S. cerevisiae* mating factor a.

The use of the mouse salivary amylase signal peptide (or a mutant thereof) to provide secretion of heterologous proteins expressed in yeast has been described in WO 89/02463 and WO 90/10075. It is the object of the present invention to provide a more efficient expression and/or secretion in yeast of heterologous proteins.

SUMMARY OF THE INVENTION

It has surprisingly been found that the signal peptide of the yeast aspartic protease 3 is capable of providing improved secretion of proteins expressed in yeast compared to the mouse salivary amylase signal peptide.

Accordingly, the present invention relates to a DNA construct comprising the following sequence 5'-P-SP- (LP)$_n$-PS-HP-3' wherein

P is a promoter sequence,

SP is a DNA sequence encoding the yeast aspartic protease 3 (YAP3) signal peptide, LP is a DNA sequence encoding a leader peptide, n is 0 or 1, PS is a DNA sequence encoding a peptide defining a yeast processing site, and HP is a DNA sequence encoding a polypeptide which is heterologous to a selected host organism.

The term "signal peptide" is understood to mean a presequence which is predominantly hydrophobic in nature and present as an N-terminal sequence of the precursor form of an extracellular protein expressed in yeast. The function of the signal peptide is to allow the heterologous protein to be secreted to enter the endoplasmic reticulum. The signal peptide is cleaved off in the course of this process. The YAP3 signal sequence has been reported previously, fused to its native gene (cf. M. Egel-Mitani et al., *Yeast* 6, 1990, pp. 127–137. A DNA construct wherein the YAP3 signal sequence is fused to a DNA sequence encoding a heterologous polypeptide is believed to be novel. The YAP3 signal peptide has not previously been reported to provide efficient secretion of heterologous polypeptides in yeast.

In the present context, the expression "leader peptide" is understood to indicate a peptide whose function is to allow the heterologous polypeptide to be directed from the endoplasmic reticulum to the Golgi apparatus and further to a secretory vesicle for secretion into the medium, (i.e. export of the expressed polypeptide across the cell wall or at least through the cellular membrane into the periplasmic space of the cell).

The expression "heterologous polypeptide" is intended to indicate a polypeptide which is not produced by the host yeast organism in nature.

In another aspect, the present invention relates to a recombinant expression vector comprising the DNA construct of the invention.

In a further aspect, the present invention relates to a cell transformed with the recombinant expression vector of the invention.

In a still further aspect, the present invention relates to a method of producing a heterologous polypeptide, the method comprising culturing a cell which is capable of expressing a heterologous polypeptide and which is transformed with a DNA construct of the invention in a suitable medium to obtain expression and secretion of the heterologous polypeptide, after which the heterologous polypeptide is recovered from the medium.

DETAILED DESCRIPTION OF THE INVENTION

In a specific embodiment, the YAP3 signal peptide is encoded by the following DNA sequence ATG AAA CTG AAA ACT GTA AGA TCT GCG GTC CTT TCG TCA CTC TTT GCA TCT CAG GTC CTT GCG(SEQ ID No: 1)

or a suitable modification thereof encoding a peptide with a high degree of homology (at least 60%, more preferably at least 70%, sequence identity) to the YAP3 signal peptide. Examples of suitable modifications" are nucleotide substitutions which do not give rise to another amino acid sequence of the peptide, but which may correspond to the codon usage of the yeast organism into which the DNA sequence is introduced, or nucleotide substitutions which do give rise to a different amino acid sequence of the peptide (although the amino acid sequence should not modified to the extent that it is no longer able to function as a signal peptide). Other examples of possible modifications are insertion of three or multiples of three nucleotides at either end of or within the sequence, or deletion of three or multiples of three nucleotides at either end of or within the sequence.

In the sequence 5'-P-SP-(LP)$_n$-PS-HP-3', n is preferably 1. In other words, although the YAP3 signal peptide may, in some instances, in itself provide secretion and/or processing of the heterologous polypeptide, a leader or pro-peptide sequence is preferably present. The leader may be a yeast MFα1 leader peptide or a synthetic leader peptide, e.g. one of the leader peptides disclosed in WO 89/02463 or WO 92/11378 or a derivative thereof capable of effecting secretion of a heterologous polypeptide in yeast. The term "synthetic" is intended to indicate that the leader peptides in question are not found in nature. Synthetic yeast leader peptides may, for instance be constructed according to the procedures described in WO 89/02463 or WO 92/11378.

The yeast processing site encoded by the DNA sequence PS may suitably be any paired combination of Lys and Arg, such as Lys-Arg, Arg-Lys, Lys-Lys or Arg-Arg, which permits processing of the heterologous polypeptide by the KEX2 protease of *Saccharomyces cerevisiae* or the equivalent protease in other yeast species (D. A. Julius et al., *Cell* 37, 1984, 1075 ff.). If KEX2 processing is not convenient, e.g. if it would lead to cleavage of the polypeptide product, a processing site for another protease may be selected instead comprising an amino acid combination which is not found in the polypeptide product, e.g. the processing site for FX$_a$, Ile-Glu-Gly-Arg (cf. Sambrook, Fritsch and Maniatis, *Molecular Cloning: A Laboratory Manual*, Cold Spring Harbor, N.Y., 1989).

The heterologous protein produced by the method of the invention may be any protein which may advantageously be produced in yeast. Examples of such proteins are aprotinin, tissue factor pathway inhibitor or other protease inhibitors, insulin or insulin precursors, human or bovine growth hormone, interleukin, glucagon, tissue plasminogen activator, transforming growth factor α or β, platelet-derived growth factor, enzymes, or a functional analogue thereof. In the present context, the term "functional analogue" is meant to indicate a polypeptide with a similar function as the native protein (this is intended to be understood as relating to the nature rather than the level of biological activity of the native protein). The polypeptide may be structurally similar to the native protein and may be derived from the native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Such modifications are well known for several of the proteins mentioned above.

The DNA construct of the invention may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned into the yeast expression vector. It should be noted that the sequence 5'-P-SP-(LP)$_n$-PS-HP-3' need not be prepared in a single operation, but may be assembled from two or more oligonucleotides prepared synthetically in this fashion.

One or more parts of the DNA sequence 5'-P-SP-(LP)$_n$-PS-HP-3' may also be of genomic or cDNA origin, for instance obtained by preparing a genomic or cDNA library and screening for DNA sequences coding for said parts (typically HP) by hybridization using synthetic oligonucleotide probes in accordance with standard techniques (cf. Sambrook, Fritsch and Maniatis, *Molecular Cloning: A Laboratory Manual*, Cold Spring Harbor, N.Y., 1989). In this case, a genomic or cDNA sequence encoding a signal peptide may be joined to a genomic or cDNA sequence encoding the heterologous protein, after which the DNA sequence may be modified by the insertion of synthetic oligonucleotides encoding the sequence 5'-P-SP-(LP)$_n$-PS-HP-3' in accordance with well-known procedures.

Finally, the DNA sequence 5'-P-SP-(LP)$_n$-PS-HP-3' may be of mixed synthetic and genomic, mixed synthetic and cDNA or mixed genomic and cDNA origin prepared by annealing fragments of synthetic, genomic or cDNA origin (as appropriate), the fragments corresponding to various parts of the entire DNA sequence, in accordance with standard techniques. Thus, it may be envisaged that the DNA sequence encoding the signal peptide or the heterologous polypeptide may be of genomic or cDNA origin, while the sequence 5'-P-SP-(LP)$_n$-PS may be prepared synthetically.

The recombinant expression vector carrying the sequence 5'-P-SP-(LP)$_n$-PS-HP-3' may be any vector which is capable of replicating in yeast organisms. In the vector, the promoter sequence (P) may be any DNA sequence which shows transcriptional activity in yeast and may be derived from genes encoding proteins either homologous or heterologous to yeast. The promoter is preferably derived from a gene encoding a protein homologous to yeast. Examples of suitable promoters are the *Saccharomyces cerevisiae* MFα1, TPI, ADH I, ADH II or PGK promoters, or corresponding promoters from other yeast species, e.g. *Schizosaccharomyces pombe*. Examples of suitable promoters are described by, for instance, Russell and Hall, *J. Biol. Chem.* 258, 1983, pp. 143–149; Russell, *Nature* 301, 1983, pp. 167–169; Ammerer, *Meth. Enzymol.* 101, 1983, pp. 192–201; Russell et al., *J. Biol. Chem.* 258, 1983, pp. 2674–2682; Hitzeman et al, *J. Biol. Chem.* 225, 1980, pp. 12073–12080; Kawasaki and Fraenkel, *Biochem. BioDhys. Res. Comm.* 108, 1982, and T. Alber and G. Kawasaki, *J. Mol. Appl. Genet.* 1, 1982, pp. 419–434.

The sequences indicated above should also be operably connected to a suitable terminator, e.g. the TPI terminator (cf. T. Alber and G. Kawasaki, *J. Mol. Genet.* 1, 1982, pp. 419–434), or the yeast CYC1 terminator.

The recombinant expression vector of the invention further comprises a DNA sequence enabling the vector to replicate in yeast. Examples of such sequences are the yeast plasmid 2μ replication genes REP 1–3 and origin of replication. The vector may also comprise a selectable marker, e.g. the *Schizosaccharomyces pombe* TPI gene as described by P. R. Russell, *Gene* 40, 1985, pp. 125–130, or the yeast URA3 gene.

The procedures used to insert the sequence 5'-P-SP-(LP)$_n$-PS-HP-3' into a suitable yeast vector containing the information necessary for yeast replication, are well known to persons skilled in the art (cf., for instance, Sambrook, Fritsch and Maniatis, op.cit.). It will be understood that the vector may be constructed either by first preparing a DNA construct containing the entire sequence and subsequently inserting this fragment into a suitable expression vector, or by sequentially inserting DNA fragments containing genetic information for the individual elements (such as the promoter sequence, the signal sequence, the leader sequence, or DNA coding for the heterologous polypeptide) followed by ligation.

The yeast organism transformed with the vector of the invention may be any suitable yeast organism which, on cultivation, produces large amounts of the heterologous polypeptide in question. Examples of suitable yeast organisms may be strains pf Saccharomyces, such as *Saccharomyces cerevisiae*, *Saccharomyces kluyveri*, or *Saccharomyces uvarum*, Schizosaccharomyces, such as *Schizosaccharomyces pombe*, Kluyveromyces, such as *Kluyveromyces lactis*, Yarrowia, such as *Yarrowia lipolytica*, or Hansenula, such as *Hansenula polymorpha*. The transformation of the yeast cells may for instance be effected by protoplast formation followed by transformation in a manner known per se.

The medium used to cultivate the cells may be any conventional medium suitable for growing yeast organisms. The secreted heterologous protein, a significant proportion of which will be present in the medium in correctly processed form, may be recovered from the medium by conventional procedures including separating the yeast cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

BRIEF DESCRIPTION OF THE DRAWINGS

The invention is further described in the following examples with reference to the appended drawings wherein FIG. 1A and 1B schematically show the construction of plasmid pLaC257;

FIG. 2 shows the DNA sequence and derived amino acid sequence of the EcoRI-XbaI insert in pLaC257 (SEQ ID No: 2);

FIG. 4 shows the DNA sequence and derived amino acid sequence of the EcoRI-XbaI fragment of pAPRSc1, wherein the protein sequence shown in italics is derived from the random expression cloned DNA fragment (SEQ ID No: 4);

FIG. 6 shows the DNA sequence and derived amino acid sequence of the EcoRI-XbaI fragment of pLaC263 (SEQ ID No: 6);

FIG. 7A and 7B show the DNA sequence and derived amino acid sequence of human tissue factor pathway inhibitor (TFPI) including its native signal peptide (SEQ ID No: 8)

FIG. 8A shows the DNA sequence and derived amino acid sequence of the spx3 signal peptide and 212 leader peptide (shown in WO 89/02463) N-terminally fused to the TFPI sequence in plasmid pYES-212 TFPI161-117Q (SEQ ID No: 10);

FIG. 8B shows the DNA sequence and derived amino acid sequence of the YAP3 signal peptide and 212 leader peptide N-terminally fused to the TFPI sequence in plasmid pYES-yk TFPI161-117Q (SEQ ID No: 12)

Figure 1A:
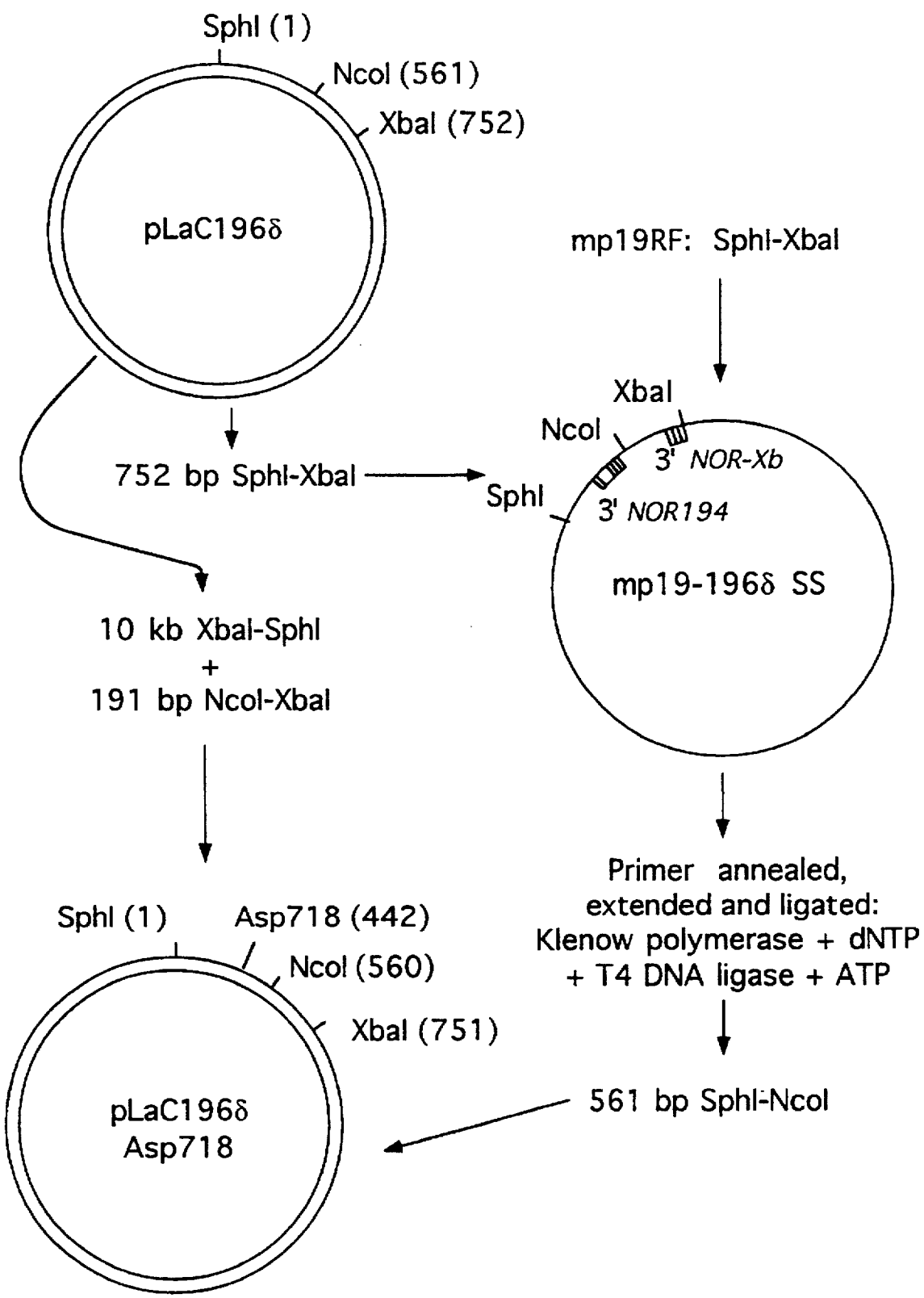

The invention is further illustrated in the following examples which are not in any way intended to limit the scope of the invention as claimed.

EXAMPLES

Plasmids and DNA materials

All expression plasmids contain 2μ DNA sequences for replication in yeast and use either the *S. cerevisiae* URA3 gene or the *Schizosaccharomyces pombe* triose phosphate isomerase gene (POT) as selectable markers in yeast. POT plasmids are described in EP patent application No. 171 142. A plasmid containing the POT-gene is available from a deposited *E. coli* strain (ATCC 39685). The POT plasmids furthermore contain the *S. cerevisiae* triose phosphate isomerase promoter and terminator ($P_{TPI}$ and $T_{TPI}$). They are identical to pMT742 (M. Egel-Mitani et al., *Gene* 73, 1988, pp. 113–120) (see FIG. 1) except for the region defined by the Sph-XbaI restriction sites encompassing the $P_{TPI}$ and the coding region for signal/leader/product. The URA3 plasmide use $P_{TPI}$ and the iso-I-cytochrome C terminator ($T_{cyc1}$).

The $P_{TPI}$ has been modified with respect to the sequence found in pMT742, only in order to facilitate construction work. An internal SphI restriction site has been eliminated by SphI cleavage, removel of single stranded tails and religation. Furthermore, DNA sequences, upstream to and without any impact on the promoter, have been removed by Ba131 exonuclease treatment followed by addition of an SphI restriction site linker. This promoter construction present on a 373 bp SphI-EcoRI fragment is designated P$_{TPI\delta}$ and when used in plasmids already described this promoter modification is indicated by the addition of a δ to the plasmid name.

Finally a number of synthetic DNA fragments have been employed all of which were synthesized on an automatic DNA synthesizer (Applied Biosystems model 380A) using phosphoramidite chemistry and commercially available reagents (S. L. Beaucage and M. H. Caruthers (1981) Tetrahedron Letters 22, 1859–1869). The oligonucleotides were purified by polyacrylamide gel electrophoresis under denaturing conditions. Prior to annealing complementary pairs of such DNA single strands these were kinased by T4 polynucleotide kinase and ATP.

All other methods and materials used are common state of the art knowledge (J. Sambrook et al., Molecular Cloning, A Laboratory Manual, Cold Spring Harbor Laboratory Press) Cold Spring Harbor, N.Y. 1989).

Example 1

The modified mouse salivary amylase signal peptide (MSA3$_{SP}$) (described in WO 89/02463) of the expression cassette of plasmid pLSC6315D3 (described in Example 3 of WO 92/11378) which contains a DNA sequence coding for the insulin precursor MI3 (B(1–29)-Ala-Ala-Lys-A (1–21)), was replaced with the YAP3 signal peptide in the following steps:

A construct for easy exchange of signal peptides was made. Through site-directed mutagenesis an Asp718 site was introduced just prior to the signal initiation codon in pLaC1966 (cf. WO 89/02463, FIG. 5), by the double primer method applying a mutagenic primer NOR494:

3'-ATTTGCTGCCATGGTACTTTCAGAAGG (SEQ ID No: 14)

where bold letters indicate mutations and the underlined sequence indicates the initiation codon.

Figure 1B:
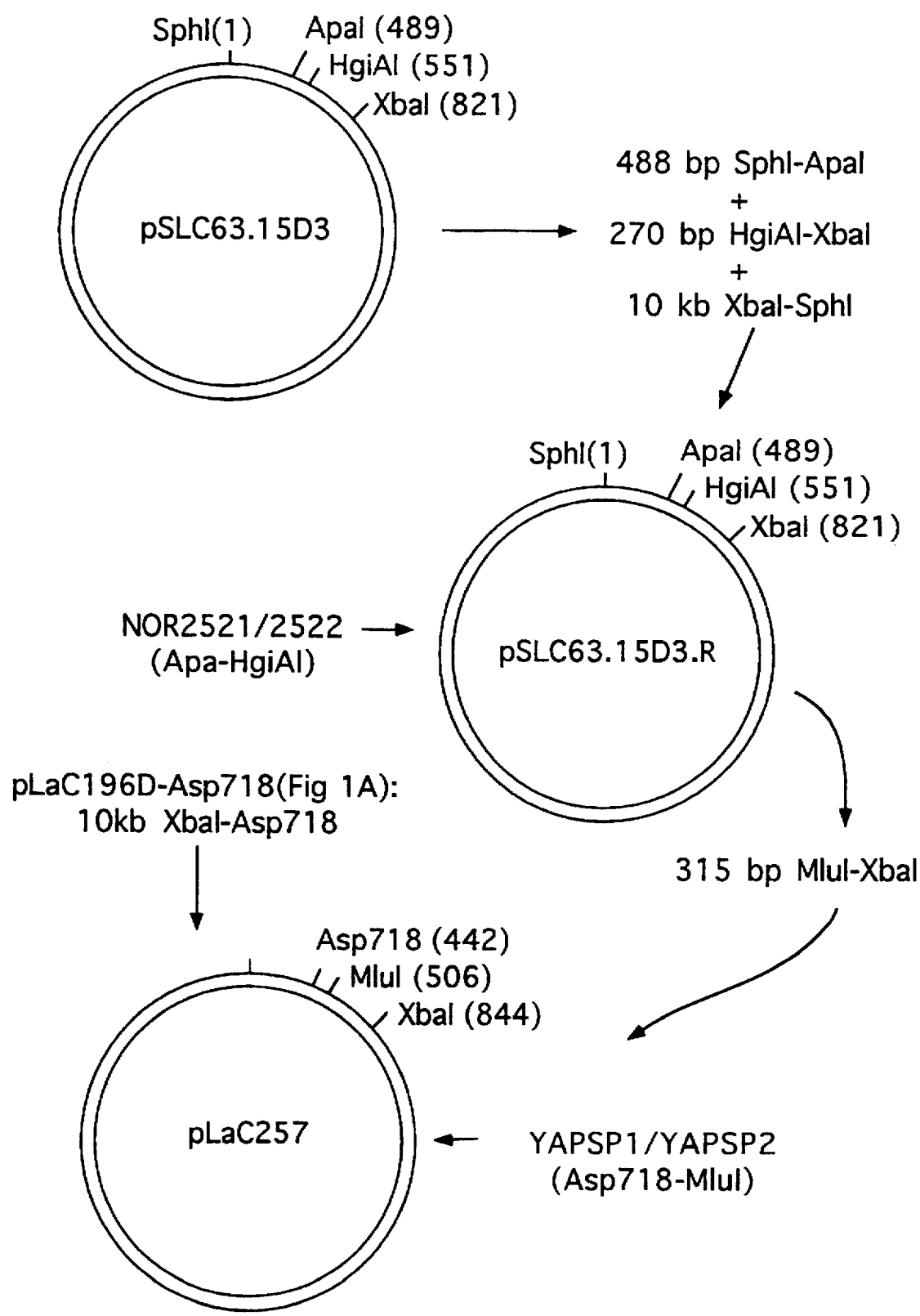

The resulting plasmid was termed pLaC1966-Asp718 (see FIG. 1).

The nucleotide sequence of the region covering the junction between signal peptide and leader peptide of the expression cassette in pLSC6315D3 was modified, by replacing the Apa1-HgiAI restriction fragment with a synthetic DNA stretch, NOR 2521/2522:

NOR2521: 5'-CAA CCA ATA GAC ACG CGT AAA GAA GGC
CTA CAG CAT GAT TAC GAT ACA GAG ATC
TTG GAG (SEQ ID No: 15)

NOR2522: 5'-C CAA GAT CTC TGT ATC GTA ATC ATG CTG
TAG GCC TTC TTT ACG CGT GTC TAT TGG
TTG GGC C (SEQ ID No: 16)

The resulting plasmid was termed pLSC6315D3R (see FIG. 1).

The SphI-Asp718 fragment of pLaC1966-Asp718 was ligated with Sph1-Mlu1 cut pLSC6315D3R plasmid and a synthetic stretch of DNA encoding the YAP3 signal peptide:

YAP-sp1: 5'-GT ACC AAA ATA ATG AAA CTG AAA ACT GTA
AGA
TCT GCG GTC CTT TCG TCA CTC TTT GCA TCT CAG GTC
CTT GGC CAA CCA ATA GAC A (SEQ ID NO: 17)

YAP-sp2: 5'-CG CGT GTC TAT TGG TTG GCC AAG GAC
CTG AGA TGC AAA GAG TGA CGA AAG GAC CGC AGA
TCT TAC AGT TTT CAG TTT CTA TAT TTTSBQ ID No: 18)

The resulting plasmid pLaC257 essentially consists of pLSC6315D3, in which the MSA3 signal peptide has been replaced by the YAP3 signal peptide (see FIG. 2).

Yeast transformation: S. cerevisiae strain MT663 (E2-7B XE11-36 a/α, Δtpi/Δtpi, pep 4-3/pep 4-3) (the yeast strain MT663 was deposited in the Deutsche Sammlung von Mikroorganismen und Zellkulturen in connection with filing WO 92/11378 and was given the deposit number DSM 6278) was grown on YPGaL (1% Bacto yeast extract, 2% Bacto peptone, 2% galactose, 1% lactate) to an O.D. at 600 nm of 0.6.

100 ml of culture was harvested by centrifugation, washed with 10 ml of water, recentrifugated and resuspended in 10 ml of a solution containing 1.2 M sorbitol, 25 mM Na$_2$EDTA pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM Na$_2$EDTA, 0.1M sodium citrate, pH 0 5.8, and 2 mg Novozym®234. The suspension was incubated at 30° C. for 30 minutes, the cells collected by centrifugation, washed in 10 ml of 1.2M sorbitol and 10 ml of CAS (1.2M sorbitol, 10 mM CaCl$_2$, 10 mM Tris HCl (Tris=Tris(hydroxymethyl)aminomethane) pH=7.5) and resuspended in 2 ml of CAS. For transformation, 1 ml of CAS-suspended cells was mixed with approx. 0.1 µg of plasmid pLaC257 and left at room temperature for 15 minutes. 1 ml of (20% polyethylene glycol 4000, 20mM CaCl$_2$, 10mM CaCl$_2$, 10mM Tris HCl, pH=7.5) was added and the mixture left for a further 30 minutes at room temperature. The mixture was centrifuged and the pellet resuspended in 0.1 ml of SOS (1.2M sorbitol, 33% v/v YPD, 6.7 mM CaCl$_2$, 14 µg/ml leucine) and incubated at 30° C. for 2 hours. The suspension was then centrifuged and the pellet resuspended in 0.5 ml of 1.2M sorbitol. Then, 6 ml of top agar (the SC medium of Sherman et al., Methods in Yeast Genetics, Cold Spring Harbor Laboratory (1982) containing 1.2 M sorbitol plus 2.5% agar) at 52° C. was added and the suspension poured on top of plates containing the same agar-solidified, sorbitol containing medium.

Transformant colonies were picked after 3 days at 30° C., reisolated and used to start liquid cultures. One transformant was selected for further characterization.

Fermentation: Yeast strain MT663 transformed with plasmid pLaC257 was grown on YPD medium (1% yeast extract, 2% peptone (from Difco Laboratories), and 3% glucose). A 1 liter culture of the strain was shaken at 30° C. to an optical density at 650 nm of 24. After centrifugation the supernatant was isolated.

MT663 cells transformed with plasmid pLSC6315D3 and cultured as described above were used for a comparison of yields of MI3 insulin precursor. Yields of MI3 were determined directly on culture supernatants by the method of Snel, Damgaard and Mollerup, Chromatographia 24, 1987, pp. 329–332. The results are shown below.

| plasmid | MI3 yield |
| --- | --- |
| pSLC63.15D3 (Msa3$_{SP}$) | 100% |
| pLaC257 (YAP3) | 120% |

Example 2

Figure 3A:
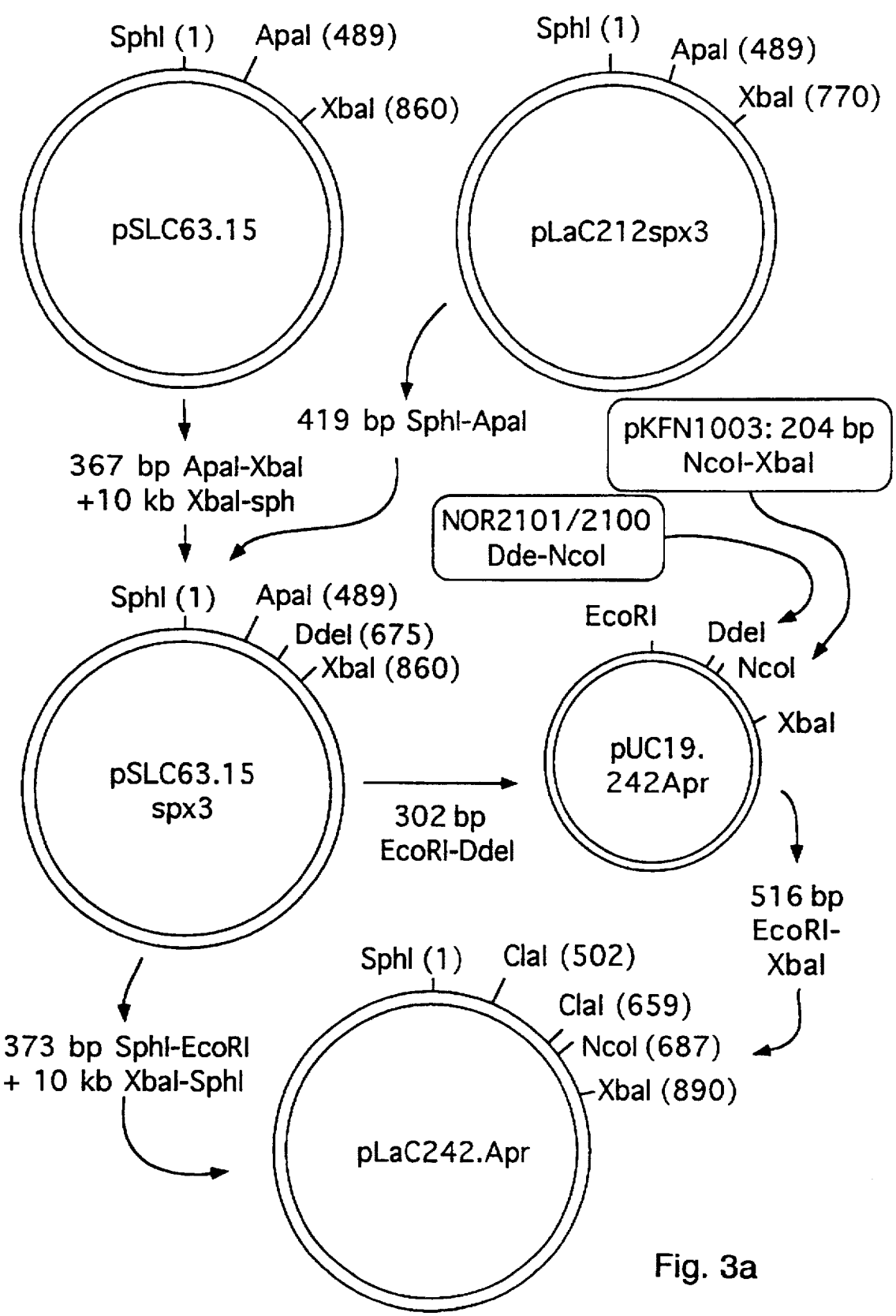
FIG. 3A and 3B schematically show the construction of plasmid pLaC242Apr.
Figure 3B:
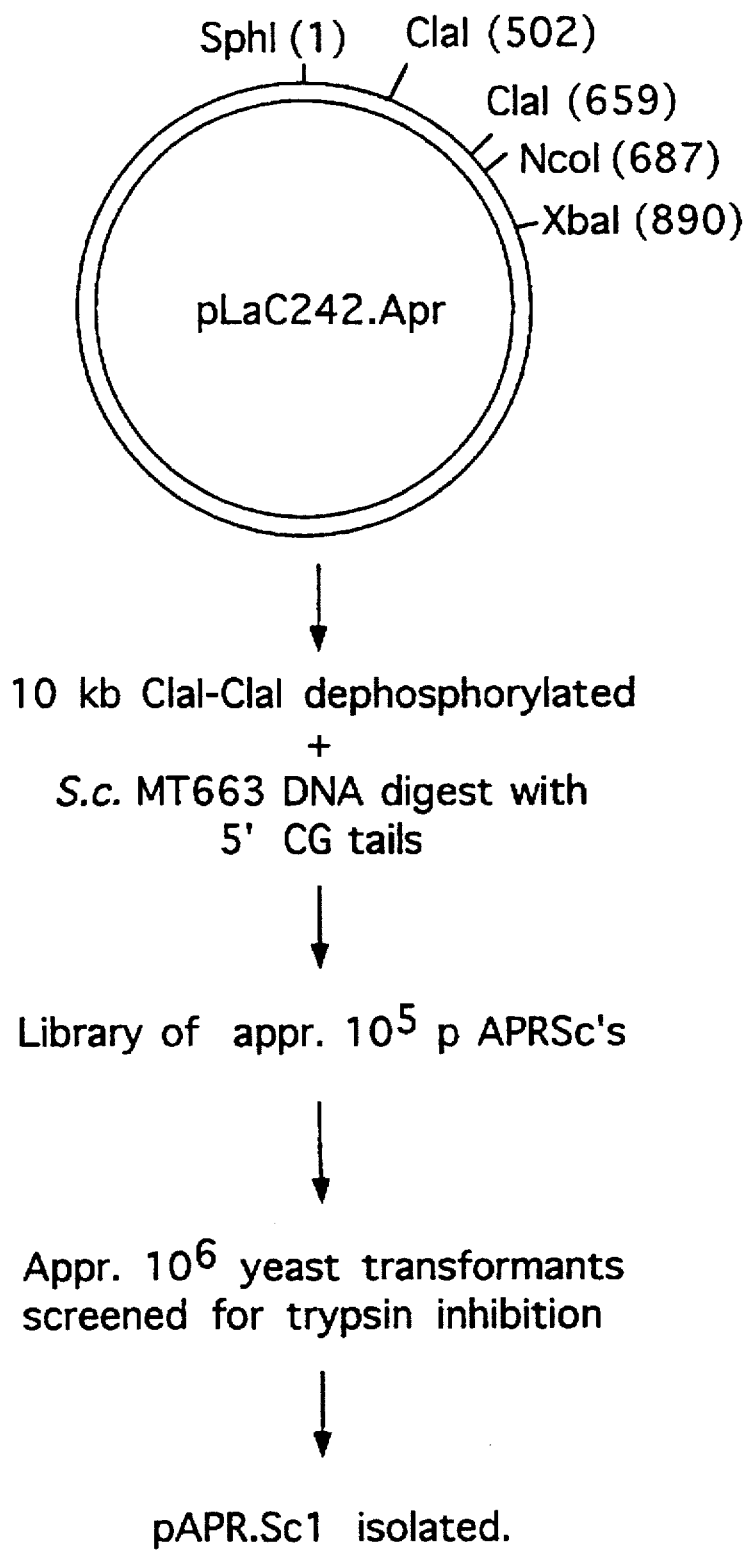

Plasmid pLSC6315D3 was modified in two steps. First, the MSA3 signal peptide was replaced by the spx3 signal peptide by exchanging the Sph1-Apa1 fragment with the analogous fragment from pLaC212spx3 (cf. WO 89/02463). From the resulting plasmid pSLC63.15spx3, a 302bp EcoR1-DdeI fragment was isolated and fused to the 204 bp NcoI-XbaI fragment of pKFN1003 (WO 90/10075) containing the DNA sequence encoding aprotinin via a synthetic linker DNA, NOR2101/2100 (see FIG. 3)

NOR2101: 5'-T AAC GTC GC (SEQ ID No: 19)

NOR2100: 5'-CAT GGC GAC G (SEQ ID No: 20)

The resulting plasmid, pLaC242-Apr (see FIG. 3), was cleaved with Cla1, dephosphorylated and applied in cloning of random 5'-CG-overhang fragments of DNA isolated from S. cerevisiae strain MT663, according to the description in WO 92/11378. Transformation and fermentation of yeast strain MT663 was carried out as described in Example 1.

From the resulting library yeast transformants harbouring the plasmid pAPR-Sc1 (prepared by the method described in WO 92/11378) containing a leader the sequence of which is given in FIG. 4, was selected by screening. The spx3 signal peptide of pAPR-Sc1 was replaced by the YAP3 signal peptide by fusing the Sph1-Sty1 fragment from pLaC257 with the 300 bp Nhe1-Xba1 fragment of pAPR-Sc1 via the synthetic linker DNA MH1338/1339 (see FIG. 5):

MH 1338: 5'-CTT GGC CAA CCA TCG AAA TTG AAA
CCA G (SEQ ID No: 21)

MH 1339: 5'-CT AGC TGG TTT CAA TTT CGA TGG TTG GC
(SEQ ID No: 22)

Figure 5:
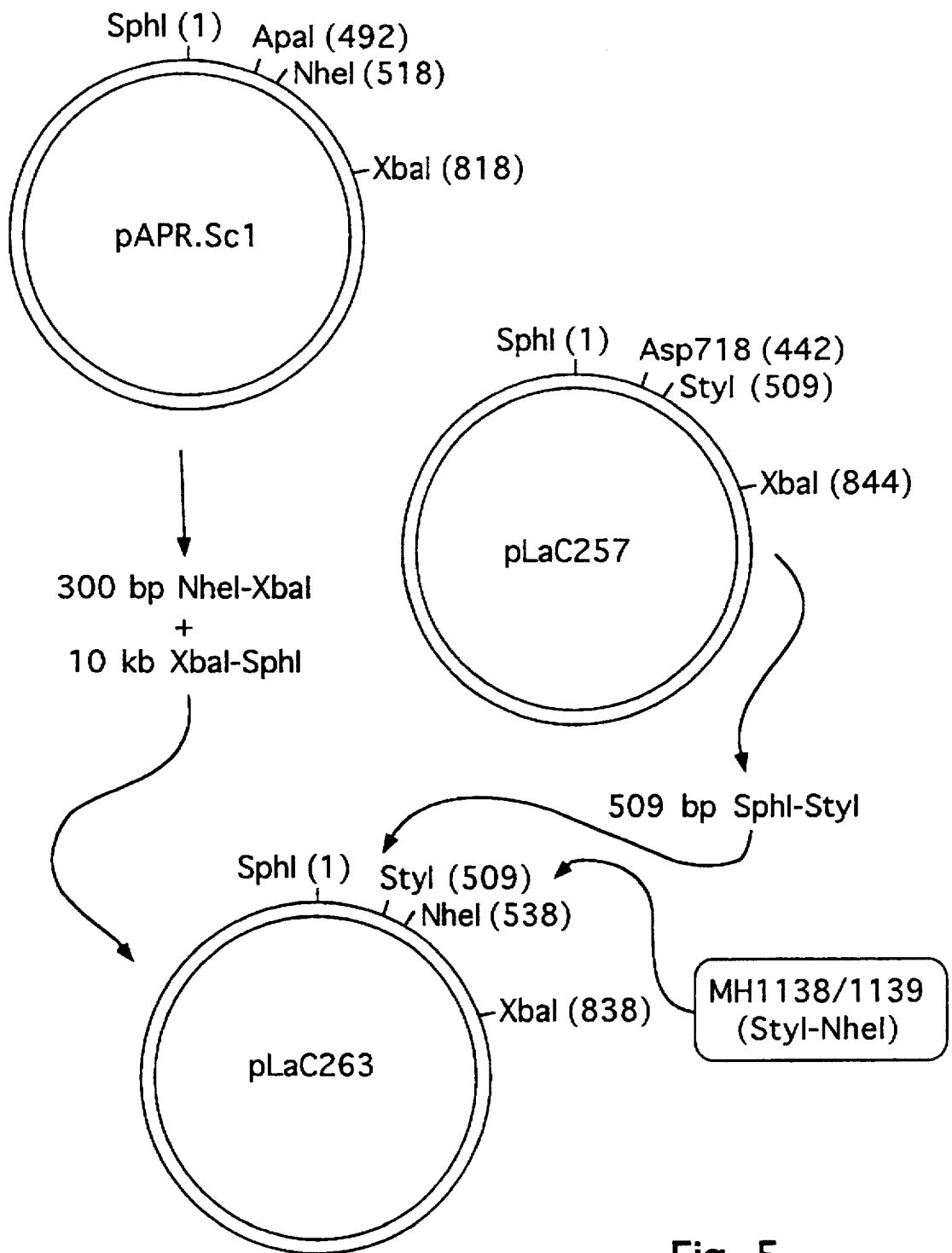
FIG. 5 schematically shows the construction of plasmid pLaC263.

The resulting plasmid was termed pLaC263 (see FIG. 5). The DNA sequence and derived amino acid sequence of the EcoRI-XbaI fragment of pLaC263 appears from FIG. 6.

| plasmid | aprotinin yield |
|---|---|
| pAPR-Sc1 (Spx3$_{SP}$) | 100% |
| pLaC263 | 136% |

Example 3

A synthetic gene coding for human TFPI, the DNA sequence of which was derived from the published sequence of a cDNA coding for human tissue factor pathway inhibitor (TFPI) (Wun et al., *J. Biol. Chem.* 263 (1988) 6001–6004), was prepared by step-wise cloning of synthetic restriction fragments into plasmid pBS(+). The resulting gene was contained on a 928 base pair (bp) SalI restriction fragment. The gene had 26 silent nucleotide substitutions in degenerate codons as compared to the cDNA resulting in fourteen unique restriction endonuclease sites. The DNA sequence of the 928 bp SalI fragment and the corresponding amino acid sequence of human TFPI (pre-form) is shown in FIG. 7 (SEQ ID No: 8).

This DNA sequence was subsequently truncated to code for a TFPI variant composed of the first 161 amino acids. A non-glycosylated variant, TFPI$_{1-161}$-117Gln in which the AAT-codon for Asn117 was replaced by CAA coding for Gln was constructed by site-directed mutagenesis in a manner known per se using synthetic oligonucleotides. The DNA sequence encoding TFPI$_{1-161}$-117Gln was preceded by the synthetic signal-leader sequence 212spx3 (cf. WO 89/02463), see FIG. 8A. This construction was inserted into the plasmid pP-212TFPI161-117Q (based on a vector of the POT-type (G. Kawasaki and L. Bell, U.S. Pat. No. 4,931, 373), cf. FIG. 8).

A 1.1 kb SphI-XbaI fragment containing the coding region for 212spx3-TFPI$_{1-161}$-117Gln was isolated and cloned into the plasmid pYES21 derived from the commercially available (Stratagene) vector pYES2.0 (cf. FIG. 8). This plasmid contains 2μ sequence for replication in yeast, the yeast URA3 gene for plasmid selection in ura3 strains, the β-lactamase gene for selection in *E. coli*, the ColE1 origin of replication for replication in *E. coli*, the f1 origin for recovery of single-stranded DNA plasmid from superinfected *E. coli* strains, and the yeast CYC1 transcriptional terminator. The SphI-XbaI fragment was cloned into pYES 2.0 in front of the CYC1 terminator. The resulting plasmid pYES-212TFPI161-117Q (cf. FIG. 9) was cleaved with PflMI and EcoRI to remove the coding region for the mouse salivary amylase signal peptide which was replaced by a double-stranded synthetic oligonucleotide sequence coding for the YAP3 signal peptide:

MHJ 1131 5'AAT TCA AAC TAA AAA ATG AAG CTT AAA
ACT GTA AGA TCT GCG GTC CTT TCG TCA CTC TTT
GCA TCG CAG GTC CTA GGT CAA CCA
GTC A (SEQ ID No: 23)

Figure 9:
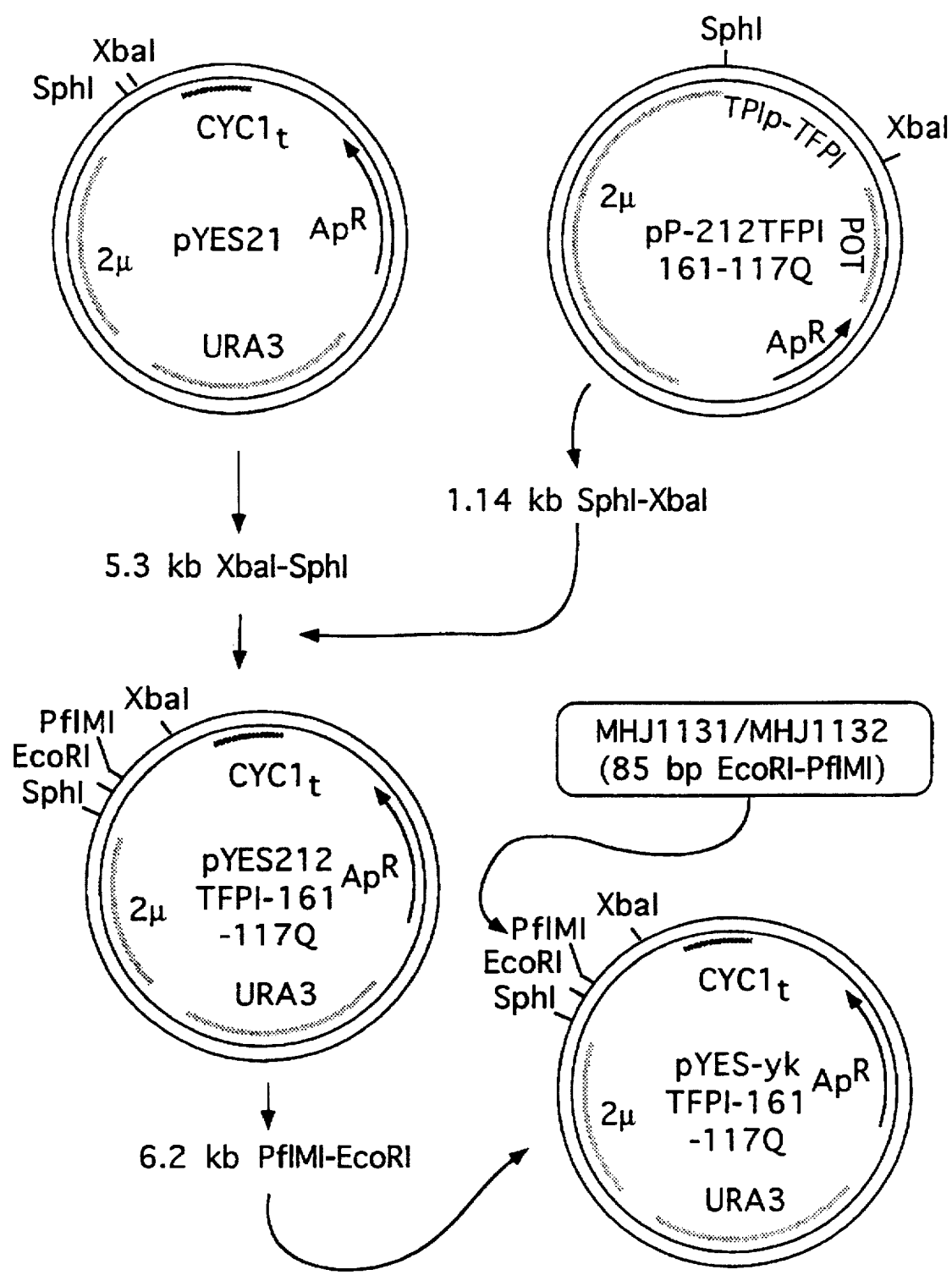
FIG. 9 shows restriction maps of plasmids pYES21, pP-212TFPI161-117Q; pYES-212TFPI161-117Q and pYES-ykTFPI161-117Q.

MHJ 1132 5'CTG GTT GAC CTA GGA CCT GCG ATG CAA
AGA GTG ACG AAA GGA CCG CAG ATC TTA CAG TTT
TAA GCT TCA TTT TTT AGT TTG (SEQ ID No: 24)

resulting in plasmid pYES-ykTFPI161-117Q (cf. FIG. 8B and FIG. 9).

Plasmids pYES-212TFPI161-117Q and pYES-ykTFPI161-117Q were transformed into the haploid yeast strain YNG318 (MATα ura3-52 leu2-Δ2pep4-Δ1 his4-539 [cir+]. Plasmid selection was for Ura+ cells. Reisolated transformants were grown in 50 ml of synthetic complete medium lacking uracil (SC-ura) for 3 days at 30° C. After measuring cell density (OD$_{600}$), the cultures were centrifuged and the resulting supernatants were analysed for the level of secreted FXa/TF/FVIIa-dependent chromogenic TFPI- activity (P.M. Sandset et al., *Thromb. Res.* 47, 1987, pp. 389–400). The mean activity measured for supernatants from strains containing plasmid pYES-212TFPI161-117Q (i.e. the plasmid containing the mouse salivary amylase signal sequence) was 0.65 U/ml•OD. The mean activity measured for supernatants from strains containing plasmid pYES-ykTFPI161-117Q was 1.00 U/ml•OD.

---

We claim:

1. A DNA construct comprising the following sequence

5'-P-SP-(LP)$_n$-PS-HP-3' wherein

P is a promoter sequence,

SP is a DNA sequence encoding the yeast aspartic protease 3 (YAP3) signal peptide, LP is a DNA sequence encoding a leader peptide, n is 0 or 1, PS is a DNA sequence encoding a peptide defining a yeast processing site, and HP is a DNA sequence encoding a polypeptide which is heterologous to a selected host organism.

2. A DNA construct according to claim 1, wherein the promoter sequence is the *Saccharomyces cerevisiae* MFα1, TPI, ADH, BAR1 or PGK promoter, or the *Schizosaccharomyces pombe* ADH promoter.

3. A DNA construct according to claim 1, wherein the YAP3 signal peptide is encoded by the following DNA sequence ATG AAA CTG AAA ACT GTA AGA TCT GCG GTC CTT TCG
TCA CTC TTT GCA TCT CAG GTC
CTT GGC                    (SEQ ID No: 1)

or a suitable modification thereof encoding a peptide with a high degree of homology to the YAP3 signal peptide.

4. A DNA construct according to claim 1, wherein n is 1.

5. A DNA construct according to claim 4, wherein the leader peptide is a yeast MFα1 leader peptide or a synthetic leader peptide.

6. A DNA construct according to claim 1, wherein PS is a DNA sequence encoding Lys-Arg, Arg-Lys, Lys-Lys, Arg-Arg or Ile-Glu-Gly-Arg.

7. A DNA construct according to claim 1, wherein the heterologous polypeptide is selected from the group consisting of aprotinin, tissue factor pathway inhibitor or other protease inhibitors, insulin or insulin precursors, human or bovine growth hormone, interleukin, glucagon, glucagon-like peptide 1, tissue plasminogen activator, transforming growth factor α or β, and platelet-derived growth factor.

8. A DNA construct according to claim 1, which further comprises a transcription termination sequence.

9. A DNA construct according to claim 8, wherein the transcription termination sequence is the TPI terminator.

10. A recombinant expression vector comprising the DNA construct of claim 1.

11. A cell transformed with a vector according to claim 10.

12. A cell according to claim 11, which is a fungal cell.

13. A cell according to claim 12, which is a yeast cell.

14. A cell according to claim 13, which is a cell of Saccharomyces, Schizosaccharomyces, Kluyveromyces, Hansenula or Yarrowia.

15. A cell according to claim 14, which is a cell of *Saccharomyces cerevisiae* or *Schizosaccharomyces pombe*.

16. A method of producing a heterologous polypeptide, comprising culturing a cell which comprises a DNA construct according to claim 10 in a suitable medium to obtain expression and secretion of the heterologous polypeptide, and recovering the heterologous polypeptide from the medium.

* * * * *

SEQUENCE LISTING ( 1 ) GENERAL INFORMATION:

( i i i ) NUMBER OF SEQUENCES: 24

( 2 ) INFORMATION FOR SEQ ID NO: 1:

( i ) SEQUENCE CHARACTERISTICS:
( A ) LENGTH: 63 base pairs (B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (vi) ORIGINAL SOURCE:
    (A) ORGANISM: Saccharomyces cerevisiae (xi) SEQUENCE DESCRIPTION: SEQ ID NO: 1:

| ATGAAACTGA | AAACTGTAAG | ATCTGCGGTC | CTTTCGTCAC | TCTTTGCATC | TCAGGTCCTT | 60 |
| GGC | | | | | | 63 |

(2) INFORMATION FOR SEQ ID NO: 2:

(i) SEQUENCE CHARACTERISTICS:
    (A) LENGTH: 476 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iii) ANTI-SENSE: NO (vi) ORIGINAL SOURCE:
    (A) ORGANISM: synthetic (ix) FEATURE:
    (A) NAME/KEY: CDS
    (B) LOCATION: 81..452

(ix) FEATURE:
    (A) NAME/KEY: sig_peptide
    (B) LOCATION: 81..293

(ix) FEATURE:
    (A) NAME/KEY: mat_peptide
    (B) LOCATION: 294..452

(xi) SEQUENCE DESCRIPTION: SEQ ID NO: 2:

```
GAATTCATTC AAGAATAGTT CAAACAAGAA GATTACAAAC TATCAATTTC ATACACAATA                      60

TAAACGACGG TACCAAAATA ATG AAA CTG AAA ACT GTA AGA TCT GCG GTC                         110
                     Met Lys Leu Lys Thr Val Arg Ser Ala Val
                     -71 -70                      -65

CTT TCG TCA CTC TTT GCA TCT CAG GTC CTT GGC CAA CCA ATA GAC ACG                        158
Leu Ser Ser Leu Phe Ala Ser Gln Val Leu Gly Gln Pro Ile Asp Thr
    -60              -55                  -50

CGT AAA GAA GGC CTA CAG CAT GAT TAC GAT ACA GAG ATC TTG GAG CAC                        206
Arg Lys Glu Gly Leu Gln His Asp Tyr Asp Thr Glu Ile Leu Glu His
-45                      -40                  -35                      -30

ATT GGA AGC GAT GAG TTA ATT TTG AAT GAA GAG TAT GTT ATT GAA AGA                        254
Ile Gly Ser Asp Glu Leu Ile Leu Asn Glu Glu Tyr Val Ile Glu Arg
                -25                  -20                      -15

ACT TTG CAA GCC ATC GAT AAC ACC ACT TTG GCT AAG AGA TTC GTT AAC                        302
Thr Leu Gln Ala Ile Asp Asn Thr Thr Leu Ala Lys Arg Phe Val Asn
            -10                      -5                   1

CAA CAC TTG TGC GGT TCC CAC TTG GTT GAA GCT TTG TAC TTG GTT TGC                        350
Gln His Leu Cys Gly Ser His Leu Val Glu Ala Leu Tyr Leu Val Cys
         5                  10                      15

GGT GAA AGA GGT TTC TTC TAC ACT CCT AAG GCT GCT AAG GGT ATT GTC                        398
Gly Glu Arg Gly Phe Phe Tyr Thr Pro Lys Ala Ala Lys Gly Ile Val
     20                  25                  30                  35
```

```
GAA CAA TGC TGT ACC TCC ATC TGC TCC TTG TAC CAA TTG GAA AAC TAC        446
Glu Gln Cys Cys Thr Ser Ile Cys Ser Leu Tyr Gln Leu Glu Asn Tyr
                 40                  45                  50

TGC AAC TAGACGCAGC CCGCAGGCTC TAGA                                      476
Cys Asn
```

( 2 ) INFORMATION FOR SEQ ID NO: 3:

( i ) SEQUENCE CHARACTERISTICS:
        ( A ) LENGTH: 124 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 3:

```
Met Lys Leu Lys Thr Val Arg Ser Ala Val Leu Ser Ser Leu Phe Ala
-71 -70              -65              -60

Ser Gln Val Leu Gly Gln Pro Ile Asp Thr Arg Lys Glu Gly Leu Gln
-55              -50              -45                          -40

His Asp Tyr Asp Thr Glu Ile Leu Glu His Ile Gly Ser Asp Glu Leu
                -35                  -30                      -25

Ile Leu Asn Glu Glu Tyr Val Ile Glu Arg Thr Leu Gln Ala Ile Asp
            -20                  -15                  -10

Asn Thr Thr Leu Ala Lys Arg Phe Val Asn Gln His Leu Cys Gly Ser
             -5              1                   5

His Leu Val Glu Ala Leu Tyr Leu Val Cys Gly Glu Arg Gly Phe Phe
 10              15                  20                       25

Tyr Thr Pro Lys Ala Ala Lys Gly Ile Val Glu Gln Cys Cys Thr Ser
             30                  35                      40

Ile Cys Ser Leu Tyr Gln Leu Glu Asn Tyr Cys Asn
             45                  50
```

( 2 ) INFORMATION FOR SEQ ID NO: 4:

( i ) SEQUENCE CHARACTERISTICS:
        ( A ) LENGTH: 450 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i i i ) ANTI-SENSE: NO ( v i ) ORIGINAL SOURCE:
        ( A ) ORGANISM: synthetic ( i x ) FEATURE:
        ( A ) NAME/KEY: CDS
        ( B ) LOCATION: 76..441

( i x ) FEATURE:
        ( A ) NAME/KEY: sig_peptide
        ( B ) LOCATION: 76..267

( i x ) FEATURE:
        ( A ) NAME/KEY: mat_peptide
        ( B ) LOCATION: 268..441

( x i ) SEQUENCE DESCRIPTION: SEQ ID NO: 4:

```
GAATTCATTC AAGAATAGTT CAAACAAGAA GATTACAAAC TATCAATTTC ATACACAATA        60

TAAACGATTA AAAGA ATG AAG GCT GTT TTC TTG GTT TTG TCC TTG ATC GGA       111
                Met Lys Ala Val Phe Leu Val Leu Ser Leu Ile Gly
```

|  |  |  |  |  | -64 |  |  |  |  | -60 |  |  |  |  | -55 |  |  |
|---|---|---|---|---|---|---|---|---|---|---|---|---|---|---|---|---|---|
| TTC | TGC | TGG | GCC | CAA | CCA | TCG | AAA | TTG | AAA | CCA | GCT | AGC | GAT | ATA | CAA | | 159 |
| Phe | Cys | Trp | Ala | Gln | Pro | Ser | Lys | Leu | Lys | Pro | Ala | Ser | Asp | Ile | Gln | | |
| | | -50 | | | | | -45 | | | | | -40 | | | | | |
| ATT | CTT | TAC | GAC | CAT | GGT | GTG | AGG | GAG | TTC | GGG | GAA | AAC | TAT | GTT | CAA | | 207 |
| Ile | Leu | Tyr | Asp | His | Gly | Val | Arg | Glu | Phe | Gly | Glu | Asn | Tyr | Val | Gln | | |
| | | -35 | | | | | -30 | | | | | -25 | | | | | |
| GAG | TTG | ATC | GAT | AAC | ACC | ACT | TTG | GCT | AAC | GTC | GCC | ATG | GCT | GAG | AGA | | 255 |
| Glu | Leu | Ile | Asp | Asn | Thr | Thr | Leu | Ala | Asn | Val | Ala | Met | Ala | Glu | Arg | | |
| -20 | | | | | | -15 | | | | | -10 | | | | | -5 | |
| TTG | GAG | AAG | AGA | AGG | CCT | GAT | TTC | TGT | TTG | GAA | CCT | CCA | TAC | ACT | GGT | | 303 |
| Leu | Glu | Lys | Arg | Arg | Pro | Asp | Phe | Cys | Leu | Glu | Pro | Pro | Tyr | Thr | Gly | | |
| | | | | 1 | | | | 5 | | | | | | 10 | | | |
| CCA | TGT | AAA | GCT | AGA | ATC | ATC | AGA | TAC | TTC | TAC | AAC | GCC | AAG | GCT | GGT | | 351 |
| Pro | Cys | Lys | Ala | Arg | Ile | Ile | Arg | Tyr | Phe | Tyr | Asn | Ala | Lys | Ala | Gly | | |
| | | | | 15 | | | | 20 | | | | | | 25 | | | |
| TTG | TGT | CAA | ACT | TTC | GTT | TAC | GGT | GGC | TGC | AGA | GCT | AAG | AGA | AAC | AAC | | 399 |
| Leu | Cys | Gln | Thr | Phe | Val | Tyr | Gly | Gly | Cys | Arg | Ala | Lys | Arg | Asn | Asn | | |
| | | 30 | | | | | 35 | | | | | | 40 | | | | |
| TTC | AAG | TCT | GCT | GAA | GAC | TGC | ATG | AGA | ACT | TGT | GGT | GGT | GCC | | | | 441 |
| Phe | Lys | Ser | Ala | Glu | Asp | Cys | Met | Arg | Thr | Cys | Gly | Gly | Ala | | | | |
| 45 | | | | | 50 | | | | | | 55 | | | | | | |

TAATCTAGA                                                                                                                       450

(2) INFORMATION FOR SEQ ID NO: 5:

(i) SEQUENCE CHARACTERISTICS:
        (A) LENGTH: 122 amino acids
        (B) TYPE: amino acid
        (D) TOPOLOGY: linear (ii) MOLECULE TYPE: protein (xi) SEQUENCE DESCRIPTION: SEQ ID NO: 5:

| Met | Lys | Ala | Val | Phe | Leu | Val | Leu | Ser | Leu | Ile | Gly | Phe | Cys | Trp | Ala |
|---|---|---|---|---|---|---|---|---|---|---|---|---|---|---|---|
| -64 | | | | -60 | | | | -55 | | | | | | -50 | |
| Gln | Pro | Ser | Lys | Leu | Lys | Pro | Ala | Ser | Asp | Ile | Gln | Ile | Leu | Tyr | Asp |
| | | | -45 | | | | -40 | | | | | | -35 | | |
| His | Gly | Val | Arg | Glu | Phe | Gly | Glu | Asn | Tyr | Val | Gln | Glu | Leu | Ile | Asp |
| | | -30 | | | | | -25 | | | | | -20 | | | |
| Asn | Thr | Thr | Leu | Ala | Asn | Val | Ala | Met | Ala | Glu | Arg | Leu | Glu | Lys | Arg |
| -15 | | | | | -10 | | | | | -5 | | | | | |
| Arg | Pro | Asp | Phe | Cys | Leu | Glu | Pro | Pro | Tyr | Thr | Gly | Pro | Cys | Lys | Ala |
| 1 | | | | 5 | | | | | 10 | | | | | 15 | |
| Arg | Ile | Ile | Arg | Tyr | Phe | Tyr | Asn | Ala | Lys | Ala | Gly | Leu | Cys | Gln | Thr |
| | | | 20 | | | | | 25 | | | | | | 30 | |
| Phe | Val | Tyr | Gly | Gly | Cys | Arg | Ala | Lys | Arg | Asn | Asn | Phe | Lys | Ser | Ala |
| | | | 35 | | | | 40 | | | | | | 45 | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 6:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: DNA (iii) HYPOTHETICAL: NO ( i i i ) ANTI-SENSE: NO ( v i ) ORIGINAL SOURCE:
    ( A ) ORGANISM: synthetic ( i x ) FEATURE:
    ( A ) NAME/KEY: CDS
    ( B ) LOCATION: 81..461

( i x ) FEATURE:
    ( A ) NAME/KEY: sig_peptide
    ( B ) LOCATION: 81..287

( i x ) FEATURE:
    ( A ) NAME/KEY: mat_peptide
    ( B ) LOCATION: 288..461

( x i ) SEQUENCE DESCRIPTION: SEQ ID NO: 6:

```
GAATTCATTC AAGAATAGTT CAAACAAGAA GATTACAAAC TATCAATTTC ATACACAATA            60

TAAACGACGG TACCAAAATA ATG AAA CTG AAA ACT GTA AGA TCT GCG GTC              110
                     Met Lys Leu Lys Thr Val Arg Ser Ala Val
                      -69              -65                  -60

CTT TCG TCA CTC TTT GCA TCT CAG GTC CTT GGC CAA CCA TCG AAA TTG            158
Leu Ser Ser Leu Phe Ala Ser Gln Val Leu Gly Gln Pro Ser Lys Leu
             -55                  -50                      -45

AAA CCA GCT AGC GAT ATA CAA ATT CTT TAC GAC CAT GGT GTG AGG GAG            206
Lys Pro Ala Ser Asp Ile Gln Ile Leu Tyr Asp His Gly Val Arg Glu
         -40                  -35                      -30

TTC GGG GAA AAC TAT GTT CAA GAG TTG ATC GAT AAC ACC ACT TTG GCT            254
Phe Gly Glu Asn Tyr Val Gln Glu Leu Ile Asp Asn Thr Thr Leu Ala
     -25                  -20                      -15

AAC GTC GCC ATG GCT GAG AGA TTG GAG AAG AGA AGG CCT GAT TTC TGT            302
Asn Val Ala Met Ala Glu Arg Leu Glu Lys Arg Arg Pro Asp Phe Cys
 -10              -5                     1                   5

TTG GAA CCT CCA TAC ACT GGT CCA TGT AAA GCT AGA ATC ATC AGA TAC            350
Leu Glu Pro Pro Tyr Thr Gly Pro Cys Lys Ala Arg Ile Ile Arg Tyr
                  10                  15                    20

TTC TAC AAC GCC AAG GCT GGT TTG TGT CAA ACT TTC GTT TAC GGT GGC            398
Phe Tyr Asn Ala Lys Ala Gly Leu Cys Gln Thr Phe Val Tyr Gly Gly
              25                  30                      35

TGC AGA GCT AAG AGA AAC AAC TTC AAG TCT GCT GAA GAC TGC ATG AGA            446
Cys Arg Ala Lys Arg Asn Asn Phe Lys Ser Ala Glu Asp Cys Met Arg
         40                      45                  50

ACT TGT GGT GGT GCC TAATCTAGA                                              470
Thr Cys Gly Gly Ala
         55
```

( 2 ) INFORMATION FOR SEQ ID NO: 7:

( i ) SEQUENCE CHARACTERISTICS:
    ( A ) LENGTH: 127 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 7:

```
Met Lys Leu Lys Thr Val Arg Ser Ala Val Leu Ser Ser Leu Phe Ala
-69              -65                  -60                  -55

Ser Gln Val Leu Gly Gln Pro Ser Lys Leu Lys Pro Ala Ser Asp Ile
             -50                  -45                      -40

Gln Ile Leu Tyr Asp His Gly Val Arg Glu Phe Gly Glu Asn Tyr Val
         -35                  -30                      -25

Gln Glu Leu Ile Asp Asn Thr Thr Leu Ala Asn Val Ala Met Ala Glu
```

```
              -20                    -15                         -10
Arg  Leu  Glu  Lys  Arg  Arg  Pro  Asp  Phe  Cys  Leu  Glu  Pro  Pro  Tyr  Thr
 -5                    1                    5                              10

Gly  Pro  Cys  Lys  Ala  Arg  Ile  Ile  Arg  Tyr  Phe  Tyr  Asn  Ala  Lys  Ala
                15                    20                         25

Gly  Leu  Cys  Gln  Thr  Phe  Val  Tyr  Gly  Gly  Cys  Arg  Ala  Lys  Arg  Asn
                30                    35                         40

Asn  Phe  Lys  Ser  Ala  Glu  Asp  Cys  Met  Arg  Thr  Cys  Gly  Gly  Ala
                45                    50                         55
```

( 2 ) INFORMATION FOR SEQ ID NO: 8:

( i ) SEQUENCE CHARACTERISTICS:
        ( A ) LENGTH: 928 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 8..919

( i x ) FEATURE:
        ( A ) NAME/KEY: sig_peptide
        ( B ) LOCATION: 8..91

( i x ) FEATURE:
        ( A ) NAME/KEY: mat_peptide
        ( B ) LOCATION: 92..919

( x i ) SEQUENCE DESCRIPTION: SEQ ID NO: 8:

```
GTCGACC ATG ATT TAC ACA ATG AAG AAA GTA CAT GCA CTT TGG GCT AGC           49
        Met Ile Tyr Thr Met Lys Lys Val His Ala Leu Trp Ala Ser
        -28         -25                 -20                 -15

GTA TGC CTG CTG CTT AAT CTT GCC CCT GCC CCT CTT AAT GCT GAT TCT           97
Val Cys Leu Leu Leu Asn Leu Ala Pro Ala Pro Leu Asn Ala Asp Ser
            -10                  -5                          1

GAG GAA GAT GAA GAA CAC ACA ATT ATC ACA GAT ACG GAG CTC CCA CCA          145
Glu Glu Asp Glu Glu His Thr Ile Ile Thr Asp Thr Glu Leu Pro Pro
            5                   10                  15

CTG AAA CTT ATG CAT TCA TTT TGT GCA TTC AAG GCG GAT GAT GGG CCC          193
Leu Lys Leu Met His Ser Phe Cys Ala Phe Lys Ala Asp Asp Gly Pro
        20                  25                  30

TGT AAA GCA ATC ATG AAA AGA TTT TTC TTC AAT ATT TTC ACT CGA CAG          241
Cys Lys Ala Ile Met Lys Arg Phe Phe Phe Asn Ile Phe Thr Arg Gln
 35                  40                  45                  50

TGC GAA GAA TTT ATA TAT GGG GGA TGT GAA GGA AAT CAG AAT CGA TTT          289
Cys Glu Glu Phe Ile Tyr Gly Gly Cys Glu Gly Asn Gln Asn Arg Phe
                55                  60                  65

GAA AGT CTG GAA GAG TGC AAA AAA ATG TGT ACA AGA GAT AAT GCA AAC          337
Glu Ser Leu Glu Glu Cys Lys Lys Met Cys Thr Arg Asp Asn Ala Asn
            70                  75                  80

AGG ATT ATA AAG ACA ACA CTG CAG CAA GAA AAG CCA GAT TTC TGC TTT          385
Arg Ile Ile Lys Thr Thr Leu Gln Gln Glu Lys Pro Asp Phe Cys Phe
         85                 90                  95

TTG GAA GAG GAT CCT GGA ATA TGT CGA GGT TAT ATT ACC AGG TAT TTT          433
Leu Glu Glu Asp Pro Gly Ile Cys Arg Gly Tyr Ile Thr Arg Tyr Phe
```

|     |     |     |     |     |     |     |     |     |     |     |     |     |     |     |     |     |
|---|---|---|---|---|---|---|---|---|---|---|---|---|---|---|---|---|
|     |     |     |     | 100 |     |     |     |     | 105 |     |     |     |     |     | 110 |     |
| TAT | AAC | AAT | CAG | ACA | AAA | CAG | TGT | GAA | AGG | TTC | AAG | TAT | GGT | GGA | TGC | 481 |
| Tyr | Asn | Asn | Gln | Thr | Lys | Gln | Cys | Glu | Arg | Phe | Lys | Tyr | Gly | Gly | Cys |     |
| 115 |     |     |     | 120 |     |     |     |     | 125 |     |     |     |     |     | 130 |     |
| CTG | GGC | AAT | ATG | AAC | AAT | TTT | GAG | ACA | CTC | GAG | GAA | TGC | AAG | AAC | ATT | 529 |
| Leu | Gly | Asn | Met | Asn | Asn | Phe | Glu | Thr | Leu | Glu | Glu | Cys | Lys | Asn | Ile |     |
|     |     |     |     | 135 |     |     |     |     | 140 |     |     |     |     |     | 145 |     |
| TGT | GAA | GAT | GGT | CCG | AAT | GGT | TTC | CAG | GTG | GAT | AAT | TAT | GGT | ACC | CAG | 577 |
| Cys | Glu | Asp | Gly | Pro | Asn | Gly | Phe | Gln | Val | Asp | Asn | Tyr | Gly | Thr | Gln |     |
|     |     |     | 150 |     |     |     |     | 155 |     |     |     |     | 160 |     |     |     |
| CTC | AAT | GCT | GTT | AAC | AAC | TCC | CTG | ACT | CCG | CAA | TCA | ACC | AAG | GTT | CCC | 625 |
| Leu | Asn | Ala | Val | Asn | Asn | Ser | Leu | Thr | Pro | Gln | Ser | Thr | Lys | Val | Pro |     |
|     |     | 165 |     |     |     |     | 170 |     |     |     |     | 175 |     |     |     |     |
| AGC | CTT | TTT | GAA | TTC | CAC | GGT | CCC | TCA | TGG | TGT | CTC | ACT | CCA | GCA | GAT | 673 |
| Ser | Leu | Phe | Glu | Phe | His | Gly | Pro | Ser | Trp | Cys | Leu | Thr | Pro | Ala | Asp |     |
| 180 |     |     |     |     | 185 |     |     |     |     | 190 |     |     |     |     |     |     |
| AGA | GGA | TTG | TGT | CGT | GCC | AAT | GAG | AAC | AGA | TTC | TAC | TAC | AAT | TCA | GTC | 721 |
| Arg | Gly | Leu | Cys | Arg | Ala | Asn | Glu | Asn | Arg | Phe | Tyr | Tyr | Asn | Ser | Val |     |
| 195 |     |     |     |     | 200 |     |     |     |     | 205 |     |     |     |     | 210 |     |
| ATT | GGG | AAA | TGC | CGC | CCA | TTT | AAG | TAC | TCC | GGA | TGT | GGG | GGA | AAT | GAA | 769 |
| Ile | Gly | Lys | Cys | Arg | Pro | Phe | Lys | Tyr | Ser | Gly | Cys | Gly | Gly | Asn | Glu |     |
|     |     |     |     | 215 |     |     |     |     | 220 |     |     |     |     |     | 225 |     |
| AAC | AAT | TTT | ACT | AGT | AAA | CAA | GAA | TGT | CTG | AGG | GCA | TGC | AAA | AAA | GGT | 817 |
| Asn | Asn | Phe | Thr | Ser | Lys | Gln | Glu | Cys | Leu | Arg | Ala | Cys | Lys | Lys | Gly |     |
|     |     |     | 230 |     |     |     |     | 235 |     |     |     |     | 240 |     |     |     |
| TTC | ATC | CAA | AGA | ATA | TCA | AAA | GGA | GGC | CTA | ATT | AAA | ACC | AAA | AGA | AAA | 865 |
| Phe | Ile | Gln | Arg | Ile | Ser | Lys | Gly | Gly | Leu | Ile | Lys | Thr | Lys | Arg | Lys |     |
|     |     | 245 |     |     |     |     | 250 |     |     |     |     | 255 |     |     |     |     |
| AGA | AAG | AAG | CAG | AGA | GTG | AAA | ATA | GCA | TAT | GAA | GAA | ATT | TTT | GTT | AAA | 913 |
| Arg | Lys | Lys | Gln | Arg | Val | Lys | Ile | Ala | Tyr | Glu | Glu | Ile | Phe | Val | Lys |     |
| 260 |     |     |     |     | 265 |     |     |     |     | 270 |     |     |     |     |     |     |
| AAT | ATG | TGAGTCGAC |     |     |     |     |     |     |     |     |     |     |     |     |     | 928 |
| Asn | Met |     |     |     |     |     |     |     |     |     |     |     |     |     |     |     |
| 275 |     |     |     |     |     |     |     |     |     |     |     |     |     |     |     |     |

( 2 ) INFORMATION FOR SEQ ID NO: 9:

( i ) SEQUENCE CHARACTERISTICS:
        ( A ) LENGTH: 304 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 9:

| Met | Ile | Tyr | Thr | Met | Lys | Lys | Val | His | Ala | Leu | Trp | Ala | Ser | Val | Cys |
|---|---|---|---|---|---|---|---|---|---|---|---|---|---|---|---|
| -28 |     |     | -25 |     |     |     | -20 |     |     |     |     | -15 |     |     |     |

| Leu | Leu | Leu | Asn | Leu | Ala | Pro | Ala | Pro | Leu | Asn | Ala | Asp | Ser | Glu | Glu |
|---|---|---|---|---|---|---|---|---|---|---|---|---|---|---|---|
|     |     | -10 |     |     |     |     | -5  |     |     |     |     | 1   |     |     |     |

| Asp | Glu | Glu | His | Thr | Ile | Ile | Thr | Asp | Thr | Glu | Leu | Pro | Pro | Leu | Lys |
|---|---|---|---|---|---|---|---|---|---|---|---|---|---|---|---|
|     | 5   |     |     |     |     | 10  |     |     |     |     | 15  |     |     |     | 20  |

| Leu | Met | His | Ser | Phe | Cys | Ala | Phe | Lys | Ala | Asp | Asp | Gly | Pro | Cys | Lys |
|---|---|---|---|---|---|---|---|---|---|---|---|---|---|---|---|
|     |     |     |     | 25  |     |     |     |     | 30  |     |     |     |     | 35  |     |

| Ala | Ile | Met | Lys | Arg | Phe | Phe | Phe | Asn | Ile | Phe | Thr | Arg | Gln | Cys | Glu |
|---|---|---|---|---|---|---|---|---|---|---|---|---|---|---|---|
|     |     |     | 40  |     |     |     |     | 45  |     |     |     |     | 50  |     |     |

| Glu | Phe | Ile | Tyr | Gly | Gly | Cys | Glu | Gly | Asn | Gln | Asn | Arg | Phe | Glu | Ser |
|---|---|---|---|---|---|---|---|---|---|---|---|---|---|---|---|
|     |     | 55  |     |     |     |     | 60  |     |     |     |     | 65  |     |     |     |

| Leu | Glu | Glu | Cys | Lys | Lys | Met | Cys | Thr | Arg | Asp | Asn | Ala | Asn | Arg | Ile |
|---|---|---|---|---|---|---|---|---|---|---|---|---|---|---|---|
|     | 70  |     |     |     |     | 75  |     |     |     |     | 80  |     |     |     |     |

| Ile | Lys | Thr | Thr | Leu | Gln | Gln | Glu | Lys | Pro | Asp | Phe | Cys | Phe | Leu | Glu |
|---|---|---|---|---|---|---|---|---|---|---|---|---|---|---|---|

-continued

| 85 | | | | 90 | | | | 95 | | | | 100 | |
|---|---|---|---|---|---|---|---|---|---|---|---|---|---|

Glu Asp Pro Gly Ile Cys Arg Gly Tyr Ile Thr Arg Tyr Phe Tyr Asn
                   105                  110                  115

Asn Gln Thr Lys Gln Cys Glu Arg Phe Lys Tyr Gly Gly Cys Leu Gly
          120                  125                  130

Asn Met Asn Asn Phe Glu Thr Leu Glu Glu Cys Lys Asn Ile Cys Glu
       135                 140                  145

Asp Gly Pro Asn Gly Phe Gln Val Asp Asn Tyr Gly Thr Gln Leu Asn
   150                  155                  160

Ala Val Asn Asn Ser Leu Thr Pro Gln Ser Thr Lys Val Pro Ser Leu
165                 170                  175              180

Phe Glu Phe His Gly Pro Ser Trp Cys Leu Thr Pro Ala Asp Arg Gly
             185                  190                195

Leu Cys Arg Ala Asn Glu Asn Arg Phe Tyr Tyr Asn Ser Val Ile Gly
         200                  205                210

Lys Cys Arg Pro Phe Lys Tyr Ser Gly Cys Gly Gly Asn Glu Asn Asn
       215               220                  225

Phe Thr Ser Lys Gln Glu Cys Leu Arg Ala Cys Lys Lys Gly Phe Ile
   230                  235                  240

Gln Arg Ile Ser Lys Gly Gly Leu Ile Lys Thr Lys Arg Lys Arg Lys
245                 250                  255              260

Lys Gln Arg Val Lys Ile Ala Tyr Glu Glu Ile Phe Val Lys Asn Met
             265                  270                275

( 2 ) INFORMATION FOR SEQ ID NO: 10:

( i ) SEQUENCE CHARACTERISTICS:
        ( A ) LENGTH: 234 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i i i ) ANTI-SENSE: NO ( v i ) ORIGINAL SOURCE:
        ( A ) ORGANISM: synthetic ( i x ) FEATURE:
        ( A ) NAME/KEY: CDS
        ( B ) LOCATION: 76..234

( i x ) FEATURE:
        ( A ) NAME/KEY: sig_peptide
        ( B ) LOCATION: 76..222

( i x ) FEATURE:
        ( A ) NAME/KEY: mat_peptide
        ( B ) LOCATION: 223..234

( x i ) SEQUENCE DESCRIPTION: SEQ ID NO: 10:

```
GAATTCATTC AAGAATAGTT CAAACAAGAA GATTACAAAC TATCAATTTC ATACACAATA          60

TAAACGATTA AAAGA ATG AAG GCT GTT TTC TTG GTT TTG TCC TTG ATC GGA         111
                Met Lys Ala Val Phe Leu Val Leu Ser Leu Ile Gly
                -49             -45                     -40

TTC TGC TGG GCC CAA CCA GTC ACT GGC GAT GAA TCA TCT GTT GAG ATT         159
Phe Cys Trp Ala Gln Pro Val Thr Gly Asp Glu Ser Ser Val Glu Ile
        -35             -30                     -25

CCG GAA GAG TCT CTG ATC ATC GCT GAA AAC ACC ACT TTG GCT AAC GTC         207
Pro Glu Glu Ser Leu Ile Ile Ala Glu Asn Thr Thr Leu Ala Asn Val
    -20             -15                     -10
```

```
GCC ATG GCT AAG AGA GAT TCT GAG GAA                                              234
Ala Met Ala Lys Arg Asp Ser Glu Glu
 -5                   1
```

( 2 ) INFORMATION FOR SEQ ID NO: 11:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 11:

```
Met Lys Ala Val Phe Leu Val Leu Ser Leu Ile Gly Phe Cys Trp Ala
-49              -45                 -40                 -35

Gln Pro Val Thr Gly Asp Glu Ser Ser Val Glu Ile Pro Glu Glu Ser
             -30              -25                 -20

Leu Ile Ile Ala Glu Asn Thr Thr Leu Ala Asn Val Ala Met Ala Lys
         -15              -10                  -5

Arg Asp Ser Glu Glu
 1
```

( 2 ) INFORMATION FOR SEQ ID NO: 12:

( i ) SEQUENCE CHARACTERISTICS:
        ( A ) LENGTH: 190 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i i i ) ANTI-SENSE: NO ( v i ) ORIGINAL SOURCE:
        ( A ) ORGANISM: synthetic ( i x ) FEATURE:
        ( A ) NAME/KEY: CDS
        ( B ) LOCATION: 17..190

( i x ) FEATURE:
        ( A ) NAME/KEY: sig_peptide
        ( B ) LOCATION: 17..178

( i x ) FEATURE:
        ( A ) NAME/KEY: mat_peptide
        ( B ) LOCATION: 179..190

( x i ) SEQUENCE DESCRIPTION: SEQ ID NO: 12:

```
GAATTCAAAC TAAAAA ATG AAG CTT AAA ACT GTA AGA TCT GCG GTC CTT      49
               Met Lys Leu Lys Thr Val Arg Ser Ala Val Leu
               -54              -50                 -45

TCG TCA CTC TTT GCA TCG CAG GTC CTA GGT CAA CCA GTC ACT GGC GAT    97
Ser Ser Leu Phe Ala Ser Gln Val Leu Gly Gln Pro Val Thr Gly Asp
             -40              -35                 -30

GAA TCA TCT GTT GAG ATT CCG GAA GAG TCT CTG ATC ATC GCT GAA AAC   145
Glu Ser Ser Val Glu Ile Pro Glu Glu Ser Leu Ile Ile Ala Glu Asn
         -25              -20                 -15

ACC ACT TTG GCT AAC GTC GCC ATG GCT AAG AGA GAT TCT GAG GAA       190
Thr Thr Leu Ala Asn Val Ala Met Ala Lys Arg Asp Ser Glu Glu
     -10              -5                   1
```

( 2 ) INFORMATION FOR SEQ ID NO: 13:

( i ) SEQUENCE CHARACTERISTICS:
  ( A ) LENGTH: 58 amino acids
  ( B ) TYPE: amino acid
  ( D ) TOPOLOGY: linear ( i i ) MOLECULE TYPE: protein ( x i ) SEQUENCE DESCRIPTION: SEQ ID NO: 13:

```
Met  Lys  Leu  Lys  Thr  Val  Arg  Ser  Ala  Val  Leu  Ser  Ser  Leu  Phe  Ala
-54            -50                      -45                      -40

Ser  Gln  Val  Leu  Gly  Gln  Pro  Val  Thr  Gly  Asp  Glu  Ser  Ser  Val  Glu
               -35                      -30                      -25

Ile  Pro  Glu  Glu  Ser  Leu  Ile  Ile  Ala  Glu  Asn  Thr  Thr  Leu  Ala  Asn
          -20                 -15                      -10

Val  Ala  Met  Ala  Lys  Arg  Asp  Ser  Glu  Glu
     -5                      1
```

( 2 ) INFORMATION FOR SEQ ID NO: 14:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA ( v i ) ORIGINAL SOURCE:
    ( A ) ORGANISM: synthetic ( x i ) SEQUENCE DESCRIPTION: SEQ ID NO: 14:

ATTTGCTGCC ATGGTACTTT CAGAAGG        27

( 2 ) INFORMATION FOR SEQ ID NO: 15:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: DNA ( v i ) ORIGINAL SOURCE:
    ( A ) ORGANISM: synthetic ( x i ) SEQUENCE DESCRIPTION: SEQ ID NO: 15:

CAACCAATAG ACACGCGTAA AGAAGGCCTA CAGCATGATT ACGATACAGA GATCTTGGAG        60

( 2 ) INFORMATION FOR SEQ ID NO: 16:

( i ) SEQUENCE CHARACTERISTICS:
    ( A ) LENGTH: 62 base pairs
    ( B ) TYPE: nucleic acid
    ( C ) STRANDEDNESS: single
    ( D ) TOPOLOGY: linear ( i i ) MOLECULE TYPE: DNA ( v i ) ORIGINAL SOURCE:
    ( A ) ORGANISM: synthetic ( x i ) SEQUENCE DESCRIPTION: SEQ ID NO: 16:

CCAAGATCTC TGTATCGTAA TCATGCTGTA GGCCTTCTTT ACGCGTGTCT ATTGGTTGGG        60

CC        62

( 2 ) INFORMATION FOR SEQ ID NO: 17:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i i ) MOLECULE TYPE: DNA ( v i ) ORIGINAL SOURCE:
    ( A ) ORGANISM: synthetic ( x i ) SEQUENCE DESCRIPTION: SEQ ID NO: 17:

```
GTACCAAAAT AATGAAACTG AAAACTGTAA GATCTGCGGT CCTTTCGTCA CTCTTTGCAT    60

CTCAGGTCCT TGGCCAACCA ATAGACA                                       87
```

( 2 ) INFORMATION FOR SEQ ID NO: 18:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i i ) MOLECULE TYPE: DNA ( v i ) ORIGINAL SOURCE:
    ( A ) ORGANISM: synthetic ( x i ) SEQUENCE DESCRIPTION: SEQ ID NO: 18:

```
CGCGTGTCTA TTGGTTGGCC AAGGACCTGA GATGCAAAGA GTGACGAAAG GACCGCAGAT    60

CTTACAGTTT TCAGTTTCTA TATTTG                                        87
```

( 2 ) INFORMATION FOR SEQ ID NO: 19:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( i i ) MOLECULE TYPE: DNA ( v i ) ORIGINAL SOURCE:
    ( A ) ORGANISM: synthetic ( x i ) SEQUENCE DESCRIPTION: SEQ ID NO: 19:

```
TAACGTCGC                                                            9
```

( 2 ) INFORMATION FOR SEQ ID NO: 20:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: DNA ( v i ) ORIGINAL SOURCE:
    ( A ) ORGANISM: synthetic ( x i ) SEQUENCE DESCRIPTION: SEQ ID NO: 20:

```
CATGGCGACG                                                          10
```

( 2 ) INFORMATION FOR SEQ ID NO: 21:

( i ) SEQUENCE CHARACTERISTICS:
    ( A ) LENGTH: 28 base pairs
    ( B ) TYPE: nucleic acid
    ( C ) STRANDEDNESS: single (D) TOPOLOGY: linear (ii) MOLECULE TYPE: DNA (vi) ORIGINAL SOURCE:
        (A) ORGANISM: synthetic (xi) SEQUENCE DESCRIPTION: SEQ ID NO: 21:

CTTGGCCAAC CATCGAAATT GAAACCAG                                              28

(2) INFORMATION FOR SEQ ID NO: 22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: synthetic (xi) SEQUENCE DESCRIPTION: SEQ ID NO: 22:

CTAGCTGGTT TCAATTTCGA TGGTTGGC                                              28

(2) INFORMATION FOR SEQ ID NO: 23:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: synthetic (xi) SEQUENCE DESCRIPTION: SEQ ID NO: 23:

AATTCAAACT AAAAATGAA GCTTAAAACT GTAAGATCTG CGGTCCTTTC GTCACTCTTT            60

GCATCGCAGG TCCTAGGTCA ACCAGTCA                                              88

(2) INFORMATION FOR SEQ ID NO: 24:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: synthetic (xi) SEQUENCE DESCRIPTION: SEQ ID NO: 24:

CTGGTTGACC TAGGACCTGC GATGCAAAGA GTGACGAAAG GACCGCAGAT CTTACAGTTT           60

TAAGCTTCAT TTTTTAGTTT G                                                    81